United States Patent [19]

Mohrs et al.

[11] Patent Number: 5,202,336

[45] Date of Patent: * Apr. 13, 1993

[54] ANTIFLAMMATORY QUINOLIN METHOXY PHENYLSULPHONAMIDES

[75] Inventors: Klaus Mohrs; Elisabeth Perzborn; Friedel Seuter, all of Wuppertal; Romanis Fruchtmann, Cologne; Christian Kohlsdorfer, Erftstadt, all of Fed. Rep. of Germany

[73] Assignee: Bayer Aktiengesellschaft, Leverkusen, Fed. Rep. of Germany

[*] Notice: The portion of the term of this patent subsequent to Dec. 3, 2008 has been disclaimed.

[21] Appl. No.: 729,020

[22] Filed: Jul. 12, 1991

Related U.S. Application Data

[60] Division of Ser. No. 614,329, Nov. 15, 1990, Pat. No. 5,070,096, which is a division of Ser. No. 587,594, Sep. 24, 1989, Pat. No. 5,093,340, which is a continuation of Ser. No. 402,934, Sep. 5, 1989, abandoned, which is a continuation-in-part of Ser. No. 294,958, Jan. 6, 1989, abandoned, which is a continuation of Ser. No. 94,239, Sep. 8, 1987, abandoned.

[30] Foreign Application Priority Data

Sep. 24, 1986 [DE] Fed. Rep. of Germany ....... 3632329

[51] Int. Cl.$^5$ ............................................. A61K 31/47
[52] U.S. Cl. .................................... 514/311; 514/312
[58] Field of Search ............................... 514/311, 312

[56] References Cited

U.S. PATENT DOCUMENTS

| | | | |
|---|---|---|---|
| 4,675,405 | 6/1987 | Musser et al. ................ | 546/153 |
| 4,794,188 | 12/1988 | Musser et al. ................ | 546/152 |
| 4,814,454 | 3/1989 | Misra ........................... | 546/153 |
| 4,876,346 | 12/1989 | Musser et al. ................ | 546/172 |
| 4,962,203 | 10/1990 | Young et al. ................. | 546/153 |
| 5,055,473 | 10/1991 | Arrowsmith et al. ......... | 546/171 |
| 5,070,096 | 12/1991 | Mohrs et al. ................. | 514/311 |
| 5,093,340 | 3/1992 | Mohrs et al. ................. | 514/311 |

FOREIGN PATENT DOCUMENTS 0181568  5/1986  European Pat. Off. ........... 546/152

Primary Examiner—Donald G. Daus
Attorney, Agent, or Firm—Sprung Horn Kramer & Woods

[57] ABSTRACT

New phenylsulphonamide of the formula in which

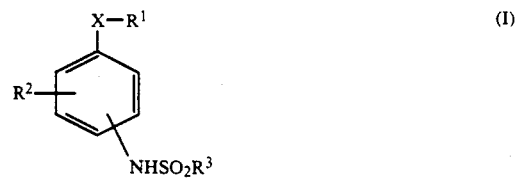

$R^1$ represents a pyridyl, quinolyl or isoquinolyl radical which is unsubstituted or substituted by halogen, alkyl, cycloalkyl, alkoxy, cyano, nitro, halogenoalkyl, halogenoalkoxy, alkoxycarbonyl or alkylsulphonyl, $R^2$ represents hydrogen, cyano, nitro, halogen, alkyl, alkoxy, halogenoalkyl, halogenoalkoxy or alkoxycarbonyl, $R^3$ represents an aryl radical which is unsubstituted or monosubstituted, disubstituted or trisubstituted by halogen, halogenoalkyl, halogenoalkoxy, alkyl, alkoxy, alkylthio, alkylsulphonyl, cyano, nitro or alkoxycarbonyl, the substituents being identical or different, or represents pentafluorophenyl or represents a straight-chain, branched or cyclic alkyl which is unsubstituted or substituted by halogen, aryl, aryloxy, cyano, alkoxycarbonyl, alkoxy, alkylthio or trifluoromethyl, and X represents an —O—, —A—B— or —B—A— group, where A denotes

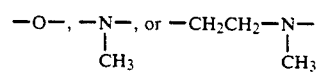

and B denotes (Abstract continued on next page.)

$-CH_2-$ or $-CH-$,
             |
            $CH_3$ where $R^1$ does not represent a pyridyl radical when X represents an —O— group, and salts thereof are prepared by reacting appropriate amines with sulphonyl halides. The substituted phenylsulphonamides can be employed as active compounds for inhibiting enzymatic reactions and for inhibiting thrombocyte aggregations.

4 Claims, No Drawings

ANTIFLAMMATORY QUINOLIN METHOXY PHENYLSULPHONAMIDES

CROSS-REFERENCES TO RELATED APPLICATIONS

This is a division of application Ser. No. 614,329, filed Nov. 15, 1990, now U.S. Pat. No. 5,070,096, which is a division of application Ser. No. 587,594, filed Sep. 24, 1989, now U.S. Pat. No. 5,093,340, which is a continuation of application Ser. No. 402,934, filed Sep. 5, 1989, now abandoned, which is a continuation-in-part of Ser. No. 294,958 filed Jan. 6, 1989, now abandoned, which is a continuation of Ser. No. 094,239 filed Sep. 8, 1987, now abandoned.

The invention relates to substituted phenylsulphonamides, a process for the preparation of these, and the use of these in medicaments.

U.S. Pat. No. 4,581,457 discloses that phenylsulphonamides having a benzimidazolylmethoxy group or a benzothiazolylmethoxy group in the aromatic ring have an antiinflammatory action.

JP 61/010,548 discloses O-pyridyl-benzlsulphonamides having an antiinflammatory and antithrombotic action, and CA 101, 110849 v describes those having a plant-protecting action.

The present invention relates to new substituted phenylsulphonamides of the general formula (I)

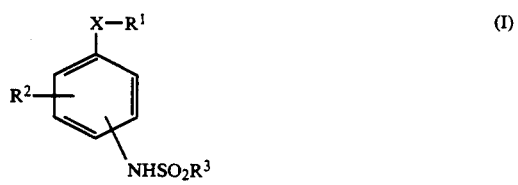

in which
- $R^1$ represents a pyridyl, quinolyl or isoquinolyl radical which may be substituted by halogen, alkyl, cycloalkyl, alkoxy, cyano, nitro, halogenoalkyl, halogenoalkoxy, alkoxycarbonyl or alkylsulphonyl,
- $R^2$ represents hydrogen, cyano, nitro, halogen, alkyl, alkoxy, halogenoalkyl, halogenoalkoxy or alkoxycarbonyl,
- $R^3$ represents an aryl radical which may be monosubstituted, disubstituted or trisubstituted by halogen, halogenoalkyl, halogenoalkoxy, alkyl, alkoxy, alkylthio, alkylsulphonyl, cyano, nitro or alkoxycarbonyl, the substituents being identical or different, or represents pentafluorophenyl or represents a straight-chain, branched or cyclic alkyl which may be substituted by halogen, aryl, aryloxy, cyano, alkoxycarbonyl, alkoxy, alkylthio or trifluoromethyl, and
- X represents a —O—, —A—B— or —B—A— group, where
  A denotes

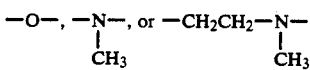

and
  B denotes

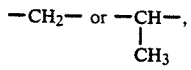

where $R^1$ does not represent a pyridyl radical when X represents an —O— group, and the salts thereof.

The substituted phenylsulphonamides according to the invention may also exist in the form of their salts. In general, salts which may be mentioned here are those with organic or inorganic acids.

In the context of the present invention, physiologically acceptable salts are preferred. Physiologically acceptable salts of the substituted phenylsulphonamides can be salts of the substances according to the invention with mineral acids, carboxylic acids or sulphonic acids. Particularly preferred salts, for example, are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Surprisingly, the substances according to the invention exhibit a good antiinflammatory and thrombocyte aggregation-inhibiting action and can be used for therapeutic treatment of humans and animals.

In general, alkyl represents a branched hydrocarbon radical having 1 to 12 carbon atoms. Lower alkyl having 1 to about 6 carbon atoms is preferred. An alkyl radical having 1 to 4 carbon atoms is particularly preferred. Examples which may be mentioned are methyl, ethyl, propyl, isopropyl, butyl, isobutyl, pentyl, isopentyl, hexyl, isohexyl, heptyl, isoheptyl, octyl and isooctyl.

In general, cycloalkyl represents a cyclic hydrocarbon radical having 5 to 8 carbon atoms. The cyclopentane and the cyclohexane ring are preferred. Examples which may be mentioned are cyclopentyl, cyclohexyl, cycloheptyl and cyclooctyl.

In general, alkoxy represents a straight-chain or branched hydrocarbon radical, having 1 to 12 carbon atoms, which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In general alkylthio represents a straight-chain or branched hydrocarbon radical, having 1 to 12 carbon atoms, which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio In general, alkylsulphonyl represents a straight-chain or branched hydrocarbon radical, having 1 to 12 carbon atoms, which is bonded via an $SO_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentylsulphonyl, hexylsulphonyl and isohexylsulphonyl.

In general, aryl represents an aromatic radical having 6 to about 12 carbon atoms. Preferred aryl radicals are phenyl, naphthyl and biphenyl.

Alkoxycarbonyl can be represented, for example, by the formula

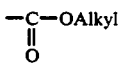

In this formula, alkyl represents a straight-chain or branched hydrocarbon radical having 1 to 12 carbon atoms. Lower alkoxycarbonyl having 1 to about 6 carbon atoms in the alkyl part is preferred. An alkoxy carbonyl having 1 to 4 carbon atoms in the alkyl part is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

In general, aryloxy represents an aromatic radical, having 6 to about 12 carbon atoms, which is bonded via an oxygen atom. Preferred aryloxy radicals are phenoxy or naphthyloxy.

In general, halogenoalkyl represents straight-chain or branched lower alkyl having 1 to 8 carbon atoms and one or more halogen atoms, preferably having one or more fluorine, chlorine and/or bromine atoms. Alkyl having 1 to 4 carbon atoms and having one or more fluorine and/or chlorine atoms is preferred. Alkyl having 1 to 2 carbon atoms and having up to 5 fluorine atoms or having up to 3 chlorine atoms is particularly preferred. Examples which may be mentioned are: fluoromethyl, chloromethyl, bromomethyl, fluoroethyl, chloroethyl, bromoethyl, fluoropropyl, chloropropyl, bromopropyl, fluorobutyl, chlorobutyl, bromobutyl, fluoroisopropyl, chloroisopropyl, bromoisopropyl, fluoroisobutyl, chloroisobutyl, bromoisobutyl, difluoromethyl, trifluoromethyl, dichloromethyl, trichloromethyl, difluoroethyl, dichloroethyl, trifluoroethyl and trichloroethyl. Trifluoromethyl, difluoromethyl, fluoromethyl and chloromethyl are very particularly preferred.

In general, halogenoalkoxy represents straight-chain or branched lower alkyl, having 1 to 8 carbon atoms and one or more halogen atoms, preferably having one or more fluorine, chlorine and/or bromine atomes, which is bonded via an oxygen atom. Halogenoalkoxy having 1 to 4 carbon atoms and having one or more fluorine and/or chlorine atoms is preferred. Halogenoalkoxy having 1 to 2 carbon atoms and having up to 5 fluorine atoms or having up to 3 chlorine atoms is particularly preferred. Examples which may be mentioned are: fluoromethoxy, chloromethoxy, fluoroethoxy, chloroethoxy, bromoethoxy, fluoropropoxy, chloropropoxy, bromopropoxy, fluorobutoxy, chlorobutoxy, bromobutoxy, fluoroisopropoxy, chloroisopropoxy, bromoisopropoxy, difluoromethoxy, dichloromethoxy, trifluoromethoxy, trichloromethoxy, difluoroethoxy, dichloroethoxy, trifluoroethoxy and trichloroethoxy. Trifluoromethoxy, difluoromethoxy, fluoromethoxy and chloromethoxy are very particularly preferred.

In general, halogen represents fluorine, chlorine, bromine or iodine, preferably fluorine, chlorine or bromine. Halogen particularly preferably represents fluorine or chlorine.

Preferred compounds of the general formula (I) are those in which $R^1$ represents a pyridyl, quinolyl or isoquinolyl radical which may be substituted by fluorine, chlorine, bromine, lower alkyl, cyclopropyl, cyclopentyl, cyclohexyl, lower alkoxy, cyano, trifluoromethyl, trifluoromethoxy, lower alkoxycarbonyl or lower alkylsulphonyl, $R^2$ represents hydrogen, cyano, nitro, fluorine, chlorine, bromine, lower alkyl, lower alkoxy, trifluoromethyl, trifluoromethoxy, or lower alkoxy carbonyl, $R^3$ represents phenyl which may be monosubstituted or disubstituted by fluorine, chlorine, bromine, trifluoromethyl, trifluoromethoxy, lower alkyl, lower alkoxy, lower alkylthio, lower alkylsulphonyl, cyano or lower alkoxycarbonyl, the substituents being identical or different, or represents pentafluorophenyl, or represents straight-chain, branched or cyclic alkyl, having up to 8 carbon atoms, which may be substituted by fluorine, chlorine, bromine, phenyl, phenoxy, cyano, lower alkoxy or trifluoromethyl, and X represents an —O—, —A—B— or —B—A— group, where
A denotes

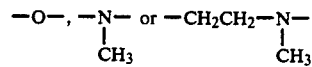

and
B denotes

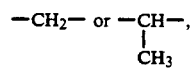

where $R^1$ cannot represent a pyridyl radical if X represents the —O— group, and the salts thereof.

Particularly preferred compounds of the general formula (I) are those in which $R^1$ represents a pyridyl, quinolyl or isoquinolyl radical which may be substituted by fluorine, chlorine, alkyl having up to 4 carbon atoms, alkoxy having up to 4 carbon atoms or by trifluoormethyl, $R^2$ represents hydrogen, cyano, fluorine, chlorine, methyl, ethyl, propyl, isopropyl, methoxy, ethoxy, trifluoromethyl, methoxycarbonyl, ethoxycarbonyl or propoxycarbonyl, $R^3$ represents phenyl which may be substituted by fluorine, chlorine, trifluoromethyl, trifluoromethoxy, alkyl having up to 4 carbon atoms, alkoxy having up to 4 carbon atoms, cyano, or alkoxycarbonyl having up to 4 carbon atoms, or represents pentafluorophenyl, or represents straight-chain or branched alkyl, having up to 6 carbon atoms, which may be substituted by fluorine, chlorine or phenyl, and X represents —O—, —OCH$_2$—, —CH$_2$O—, —OCH(CH$_3$)—, —CH$_2$N(CH$_3$)— or —CH$_2$N(CH$_3$)CH$_2$CH$_2$—, where $R^1$ cannot represent a pyridyl radical when X represents the —O— group, and the salts thereof.

Examples which may be mentioned are the following substituted phenylsulphonamides.

N-[2-(quinolin-8-yloxy)phenyl]-4-chlorobenzenesulphonamide

N-[2-(quinolin-8-yloxy)phenyl]-3-trifluoromethylbenzenesulphonamide
N-[2-(quinolin-8-yloxy)phenyl]-butanesulphonamide
N-[2-(quinolin-8-yloxy)phenyl]-3-chloropropanesulphonamide
N-[2-(quinolin-8-yloxy)phenyl]-4-fluorobenzenesulphonamide
N-[4-(quinolin-8-yloxy)phenyl]-4-chlorobenzenesulphonamide
N-[4-(quinolin-8-yloxy)phenyl]-3-trifluoromethylbenzenesulphonamide
N-[4-(quinolin-8-yloxy)phenyl]butanesulphonamide
N-[4-(quinolin-8-yloxy)phenyl]-3-chloropropanesulphonamide
N-[4-(quinolin-8-yloxy)phenyl]-4-fluorobenzenesulphonamide
N-[3-(quinolin-8-yloxy)phenyl]-4-chlorobenzenesulphonamide
N-[3-(quinolin-8-yloxy)phenyl]-3-trifluoromethylbenzenesulphonamide
N-[3-(quinolin-8-yloxy)phenyl]-4-fluorobenzenesulphonamide
N-[3-(quinolin-8-yloxy)phenyl]-3-chloropropanesulphonamide
N-[3-(quinolin-8-yloxy)phenyl]butanesulphonamide
N-[4-(quinolin-7-yloxy)phenyl]-4-chlorobenzenesulphonamide
N-[4-(quinolin-7-yloxy)phenyl]-3-trifluoromethylbenzenesulphanamide
N-[4-(quinolin-7-yloxy)phenyl]butanesulphonamide
N-[4-(quinolin-7-yloxy)phenyl]-3-chloropropanesulphonamide
N-[4-(quinolin-7-yloxy)phenyl]-4-fluorobenzenesulphonamide
N-[4-(4-methylouinolin-8-yloxy)phenyl]-4-chlorobenzenesulphonamide
N-[4-(4-methylouinolin-8-yloxy)phenyl]-3-trifluoromethylbenzenesulphonamide
N-[4-(4-methylouinolin-8-yloxy)phenyl]-butanesulphonamide
N-[4-(quinolin-8-yloxy)-3-chlorophenyl]-4-chlorobenzenesulphonamide
N-[4-(quinolin-8-yloxy)-3-chlorophenyl]-3-trifluoromethylbenzenesulphonamide
N-[4-(6-methylquinolin-8-yloxy)phenyl]butanesulphonamide
N-[4-(6-methylquinolin-8-yloxy)phenyl]-4-chlorbenzenesulphonamide
N-[2-(4-methylquinolin-8-yloxy)phenyl]-4-chlorobenzenesulphonamide
N-[2-(4-methylquinolin-8-yloxy)phenyl]butanesulphonamide
N-[4-(quinolin-6-yloxy)phenyl]-4-chlorobenzenesulphonamide
N-[4-(quinolin-6-yloxy)phenyl]-3-trifluoromethylbenzenesulphonamide
N-[4-(quinolin-6-yloxy)phenyl]butanesulphonamide
N-[2-(quinolin-6-yloxy)phenyl]-4-chlorobenzenesulphonamide
N-[2-(quinolin-6-yloxy)phenyl]butanesulphonamide
N-[4-(4-methylquinolin-2-yloxy)phenyl]-4-chlorobenzenesulphonamide
N-[4-(quinolin-2-yl-methyloxy)phenyl]-4-chlorobenzenesulphonamide
N-[4-(quinolin-2-yl-methyloxy)phenyl]-3-trifluoromethylbenzenesulphonamide
N-[4-(quinolin-2-yl-methyloxy)phenyl]butanesulphonamide
N-[4-(quinolin-2-yl-methyloxy)phenyl]-3-chloropropanesulphonamide
N-[4-(quinolin-2-yl-methyloxy)phenyl]pentafluorobenzenesulphonamide
N-[4-(quinolin-2-yl-methyloxy)phenyl]-1-methyl-butanesulphonamide
N-[2-(quinolin-2-yl-methyloxy)phenyl]-4-chlorobenzenesulphonamide
N-[2-(quinolin-2-yl-methyloxy)phenyl]-3-trifluoromethylbenzenesulphonamide
N-[2-(quinolin-2-yl-methyloxy)phenyl]butanesulphonamide
N-[2-(quinolin-2-yl-methyloxy)phenyl]-3-chloropropanesulphonamide
N-[3-(quinolin-2-yl-methyloxy)phenyl]-4-chlorobenzenesulphonamide
N-[3-(quinolin-2-yl-methyloxy)phenyl]-3-trifluoromethylbenzenesulphonamide hydrochloride
N-[3-(quinolin-2-yl-methyloxy)phenyl]butanesulphonamide
N-[3-(quinolin-2-yl-methyloxy)phenyl]-3-chloropropanesulphonamide
N-{4-[1-(quinolin-2-yl)ethyloxy[phenyl}butanesulphonamide
N-[4-(quinolin-2-yl]methyloxy-3-cyano-phenyl]-butanesulphonamide
N-[3-ethoxycarbonyl-4-(quinolin-2-yl)methyloxyphenyl]-butanesulphonamide
N-[2-(quinolin-8-yloxymethyl)phenyl]-4-chlorobenzenesulphonamide
N-[3-(quinolin-8-yloxymethyl)phenyl]-4-chlorobenzenesulphonamide
N-[3-(quinolin-8-yloxymethyl)phenyl]-3-trifluoromethylbenzenesulphonamide
N-[3-(quinolin-8-yloxymethyl)phenyl]butanesulphonamide
N-[3-(quinolin-8-yloxymethyl)phenyl]-4-fluorobenzenesulphonamide
N-[2-(quinolin-8-yloxymethyl)phenyl]butanesulphonamide
N-[2-(quinolin-8-yloxymethyl)phenyl]-3-trifluoromethylbezenesulphonamide
N-[2-(quinolin-8-yloxymethyl)phenyl]-3-chloropropanesulphonamide
N-[3-(quinolin-8-yloxymethyl)phenyl]-3-chloropropanesulphonamide
N-[2-(quinolin-8-yloxymethyl)phenyl]-4-fluorobenzenesulphonamide
N,N',N'-[3-(methyl-2-pyridyl-aminomethyl)phenyl]-butanesulphonamide
N,N',N'-[3-(methyl-2-pyridyl-aminomethyl)phenyl]-3-chloropropanesulphonamide
N,N',N'-[3-(methyl-2-pyridyl-aminomethyl)phenyl]-3-trifluoromethylbenzenesulphonamide
N,N',N'-[3-(methyl-2-pyridyl-aminomethyl)phenyl]-4-chlorobenzenesulphonamide
N,N',N'-{3-{[methyl-2-(2-pyridyl)ethyl]aminomethyl}-phenyl}-4-chlorobenzenesulphonamide
N,N',N'-{3-{[methyl-2-(2-pyridyl)ethyl]aminomethyl}-phenyl}-3-trifluoromethylbenzenesulphonamide
N,N',N'-{3-{[methyl-2-(2-pyridyl)ethyl]aminomethyl}-phenyl}-butanesulphonamide Furthermore, a process has been found for this preparation of substituted phenylsulphonamides, according to the invention, of the general formula (I)

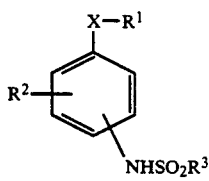

in which

R[1] represents a pyridyl, quinolyl or isoquinolyl radical which may be substituted by halogen, alkyl, cycloalkyl, alkoxy, cyano, nitro, halogenoalkyl, halogenoalkoxy, alkoxycarbonyl or alkylsulphonyl, R[2] represents hydrogen, cyano, nitro, halogen, alkyl, alkoxy, halogenoalkyl, halogenoalkoxy, or alkoxycarbonyl, R[3] represents an aryl radical which may be monosubstituted, disubstituted or trisubstituted by halogen, halogenoalkyl, halogenoalkoxy, alkyl, alkoxy, alkylthio, alkylsulphonyl, cyano, nitro or alkoxycarbonyl, the substituents being identical or different, or represents pentafluorophenyl or represents straight-chain, branched or cyclic alkyl which may be substituted by halogen, aryl, aryloxy, cyano, alkoxycarbonyl, alkoxy, alkylthio or trifluoromethyl, X represents a —O—, —A—B— or —B—A— group, where A denotes —O—, —N—, or —CH$_2$CH$_2$—N—
          |                    |
          CH$_3$               CH$_3$ and B denotes —CH$_2$— or —CH—,
             |
             CH$_3$ where R[1] cannot represent a pyridyl radical when X represents the —O— group, and the salts thereof, which is characterized in that amines of the general formula (II)

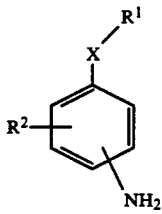

in which

R[1], R[2] and X have the abovementioned meaning, are reacted with sulphonyl halides of the general formula (III)

R[3]—SO$_2$—Y                                    (III)

in which

R[3] has the abovementioned meaning and

Y represents halogen in the presence of an inert solvent and if appropriate in the presence of a bias, and, in the case of the preparation of the salts, the product of this reaction is reacted, if appropriate, with an appropriate acid.

The process according to the invention may be illustrated by the following equation:

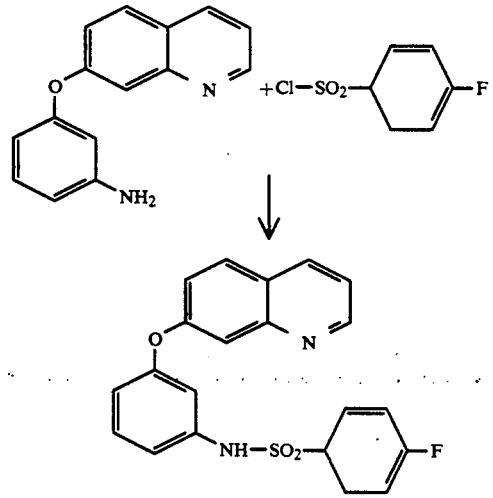

Suitable solvents for the process according to the invention are conventional organic solvents which are inert under the reaction conditions. These preferably include ethers, such as diethyl ether, dioxane, tetrahydrofuran or glycol dimethyl ether, or hydrocarbons, such as benzene, toluene, xylene, hexane, cyclohexane or petroleum reactions, or halogenated hydrocarbons, such as dichloromethane, trichloromethane, tetrachloromethane dichloroethylene, trichloroethylene or chlorobenzene, or ethyl acetate, triethylamine, pyridine, dimethyl sulphoxide dimethylformamide, hexamethylphosphoric triamide, acetonitrile, acetone or nitromethane. It is likewise possible to use mixtures of the solvents mentioned.

Bases for the process according to the invention can be conventional basic compounds. These preferably include alkali metal or alkaline-earth metal hydroxides, such as lithium hydroxide, sodium hydroxide, potassium hydroxide or barium hydroxide, or alkali metal hydrides, such as sodium hydride, or alkali metal or alkaline-earth metal carbonates, such as sodium carbonate, sodium hydrogen carbonate, potassium carbonate or calcium carbonate, or alkali metal alcoholates, such as, for example, sodium methanolate, sodium ethanolate, potassium methanolate, potassium ethanolate or potassium tert-butylate, or alkali metal amides, such as sodium amide or lithium diisopropylamide, or organic amines, such as benzyltrimethylammonium hydroxide, tetrabutylammonium hydroxide, pyridine, dimethylaminopyridine, triethylamine, N-methylpiperidine, 1,5-diazabicyclo[4,3,0]non-5-ene or 1,5-diazabicyclo[5,4,0]undec-5-ene.

The process according to the invention is generally carried out in a temperature range from −30° C. to +150° C., preferably from −20° C. to +80° C.

The process according to the invention is generally carried out at atmospheric pressure. However, it is also possible to carry out the process at superatmospheric pressure or subatmospheric pressure (for example in a range from 0.5 to 5 bar).

In general, 1 to 5 moles, preferably 1 to 2 moles, particularly preferably 1 mole, of sulphonyl halide are employed per mole of amine. The base is preferably employed in an amount from 1 to 10 moles, preferably from 1 to 5 moles, relative to the sulphonyl halide.

Sulphonyl halides which may be mentioned as examples for the process according to the invention are:
4-toluene-sulphonyl chloride
4-chlorophenyl-sulphonyl chloride
4-fluorophenyl-sulphonyl-chloride
3-trifluoromethylphenyl-sulphonyl chloride
pentafluorophenyl-sulphonyl chloride
2,5-dichlorophenyl-sulphonyl chloride
4-methoxyphenyl-sulphonyl chloride
propyl-sulphonyl chloride
butyl-sulphonyl chloride
isobutyl-sulphonyl chloride
1-methylbutyl-sulphonyl chloride
3-chloropropyl-sulphonyl chloride
4-chlorobutyl-sulphonyl chloride
pentyl-sulphonyl chloride.

The amines of the general formula (II)

(II)

in which
R$^1$ represents a pyridyl, quinolyl or isoquinolyl radical which may be substituted by halogen, alkyl, cycloalkyl, alkoxy, cyano, nitro, halogenoalkyl, halogenoalkoxy, alkoxycarbonyl or alkylsulphonyl, R$^2$ represents hydrogen, cyano, nitro, halogen, alkyl, alkoxy, halogenoalkyl, halogenoalkoxy or alkoxycarbonyl, and X represents an —O—, —A—B— or —B—A— group, where
A denotes —O—, —N—, or —CH$_2$CH$_2$—N—
     |                         |
     CH$_3$               CH$_3$ and
B denotes —CH$_2$— or —CH—,
                  |
                  CH$_3$ where R$^1$ cannot represent a pyridyl group when X represents the —O— group, can be prepared by reducing nitro compounds of the general formula (IV)

(IV)

in which
R$^1$, R$^2$ and X have the abovementioned meaning.

The process according to the invention may be illustrated by the following equation:

Reduction →

The reduction is generally carried out by hydrogenation using metal catalysts, such as, for example, platinum, palladium, palladium on animal charcoal, platinum oxide or Raney nickel, preferably using palladium on animal charcoal, in the presence of acids.

Acids which may be employed according to the invention are strong mineral acids, but alternatively organic acids. These are preferably hydrochloric acid, hydrobromic acid, sulphuric acid, phosphoric acid, or carboxylic acids, such as acetic acid, oxalic acid, trifluoroacetic acid, or sulphonic acids, such as methane sulphonic acid, ethane sulphonic acid, phenylsulphonic acid, toluenesulphonic acid or naphthalenedisulphonic acid.

The catalyst in this reduction is generally employed in an amount from 0.1 to 50 mole %, preferably from 1 to 10 mole %, relative to 1 mole of the nitro compound.

The hydrogenation is generally carried out in a temperature range from −20° C. to +100° C., preferably in the range from 0° C. to +50° C.

In general, the hydrogenation is carried out at atmospheric pressure. It is likewise possible to carry out the hydrogenation at a superatmospheric pressure of 2 to 200 bar, preferably from 2 to 50 bar.

Suitable solvents for the hydrogenation are water and inert organic solvents. These preferably include alcohols, such as, for example, methanol, ethanol, propanol, or isopropanol, or ethers, such as diethyl ether, dioxane, tetrahydrofuran, glycol monomethyl ether or glycol dimethyl ether, or chlorinated hydrocarbons such as methylene chloride, chloroform or carbon tetrachloride, or glacial acetic acid, trifluoroacetic acid, dimethylformamide, hexamethylphosphoric triamide, ethyl acetate, acetone or pyridine. It is likewise possible to employ mixtures of the solvents mentioned.

In addition, the reduction can also be carried out by methods which are generally conventional for the reduction of nitro groups to amino groups. Examples of methods which may be mentioned are: Reduction using hydrazine in water and/or alcohols, such as, for example, methanol, ethanol, propanol or isopropanol, preferably in the presence of catalysts, such as platinum, palladium or palladium on animal charcoal, in a temperature range from 0° C. to +150° C., preferably from +20° C. to +100° C.

The reduction using lithium aluminium hydride in inert solvents, such as ethers, for example diethyl ether, dioxane or tetrahydrofuran, or hydrocarbons, such as benzene, toluene or xylene, or chlorinated hydrocarbons, such as methylene chloride, chloroform or carbon tetrachloride, in a temperature range from −30° C. to +150° C., preferably from 0° C. to +80° C., or reduction using zinc in water and/or alcohols, such as methanol, ethanol, propanol or isopropanol, in the presence of acids, such as hydrochloric acid or acetic acid.

The amines used according to the invention can likewise be prepared as described, for example, in DE-A-3,607,382.

Examples of amines used according to the invention are:
8-(2-aminophenoxy)quinoline
7-(4-aminophenoxy)quinoline
8-(4-aminophenoxy)quinoline
8-(3-aminophenoxy)quinoline
8-(4-aminophenoxy)-4-methyl-quinoline
8-(4-amino-2-chlorophenoxy)quinoline
8-(4-aminophenoxy)-6-methyl-quinoline
8-(2-aminophenoxy)-4-methyl-quinoline
6-(2-aminophenoxy)quinoline
2-(4-aminophenoxymethyl)quinoline
2-(2-aminophenoxymethyl)quinoline
2-(3-aminophenoxymethyl)quinoline
2-(4-amino-2-cyano-phenoxymethyl)quinoline
2-[1-(4-aminophenoxy)ethyl]quinoline
2-(4-amino-2-ethoxycarbonyl-phenoxymethyl)quinoline
8-(2-aminobenzyloxy)quinoline
8-(3-aminobenzyloxy)quinoline
2-[N-(3-aminobenzyl)-N-methyl]aminopyridine
2-[2-(N-3-aminobenzyl-N-methyl)aminoethyl]pyridine The nitro compounds of the general formula (IV) employed as starting materials, where
a) Nitro compounds correspond to the general formula (IVa)

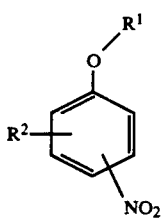

(IVa)

in which $R^1$ and $R^2$ have the meanings specified, and X represents —O—, but $R^1$ does not represent a pyridyl radical, and where
b) nitro compounds correspond to the general formula (IVb)

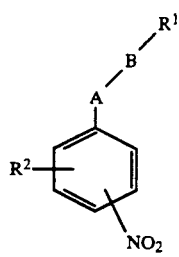

(IVb)

in which $R^1$ and $R^2$ have the meanings specified and X represents —A—B—, and where
c) nitro compounds correspond to the general formula (IVc)

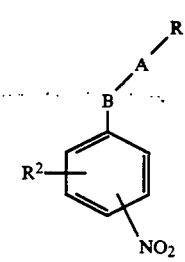

(IVc)

in which $R^1$ and $R^2$ have the meanings specified and X represents —B—A, can be prepared by reacting fluoronitrophenyl compounds of the general formula (V)

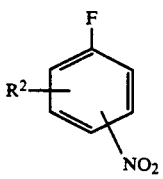

(V)

in which $R^3$ has the meaning specified, with alcohols of the general formula (VI)

$R^1$—OH  (VI)

in which $R^1$ has the meaning specified but cannot represent a pyridyl radical, in suitable solvents in the presence of bases.

The reaction may be illustrated by the following equation:

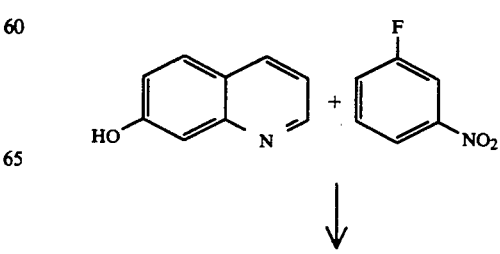

-continued

[chemical structure: quinoline with O-phenyl-NO2 substituent]

Suitable solvents are the conventional organic solvents which are inert under the reaction conditions. These preferably include ethers, such as, for example, dioxane, tetrahydrofuran or diethyl ether, or chlorinated hydrocarbons, such as methylene chloride, trichloromethane or tetrachloromethane, or hydrocarbons, such as benzene, toluene, xylene, hexane, cyclohexane, or petroleum fractions, or amides, such as dimethylformamide or hexamethylphosphoric triamide, or pyridine. It is likewise possible to employ mixtures of the solvents mentioned.

Bases which may be employed are the conventional inorganic or organic bases. These preferably include alkali metal hydroxides, such as, for example, sodium hydroxide or potassium hydroxide, or alkaline-earth metal hydroxides, such as, for example, barium hydroxide, or alkali metal carbonates, such as sodium carbonate or potassium carbonate, or alkaline-earth metal carbonates, such as calcium carbonate, or organic amines, such as triethylamine, pyridine or methylpiperidine.

The process is generally carried out in a temperature range from 0° C. to +150° C., preferably from +20° C. to +100° C.

The process is generally carried out at atmospheric pressure, but it is also possible to carry out the process at subatmospheric pressure or at superatmospheric pressure (for example in a range from 0.5 to 5 bar).

In general, 0.5 to 2 moles, preferably 1 mole, of alcohol are employed relative to 1 mole of fluoronitrophenyl compound.

Examples of fluoronitrophenyl compounds which are used according to the invention are:
2-fluoronitrobenzene,
3-fluoronitrobenzene,
4-fluoronitrobenzene.

Examples of alcohols which are used according to the invention are:
2-hydroxyquinoline,
4-hydroxyquinoline,
5-hydroxyquinoline,
8-hydroxyquinoline,
1-hydroxyisoquinoline,
5-hydroxyisoquinoline,
2-hydroxy-4-methyl-quinoline,
8-hydroxy-4-methyl-quinoline,
8-hydroxy-6-methyl-quinoline.

The compounds of the general formula (V) and (VI) used as starting materials are known.

The compounds of the general formula (IVb) are prepared by reacting nitrophenyl compounds of the general formula (VII)

[structure VII: phenyl with AH, R2, NO2 substituents] (VII)

in which
R² and A have the meaning specified,
with halides of the general formula (VIII)

$$Hal-B-R^1 \qquad (VIII)$$

in which
R¹ and B have the meaning specified and
Hal represents chlorine, bromine or iodine;
in suitable solvents, if appropriate in the presence of a base.

The process according to the invention may be illustrated, for example, by the following equation:

[reaction scheme showing 3-nitrophenol + 7-(bromomethyl)quinoline → 7-((3-nitrophenoxy)methyl)quinoline]

Suitable solvents are the conventional organic solvents which are inert under the reaction conditions. These preferably include alcohols, such as, for example, methanol, ethanol, propanol or isopropanol, or ethers, such as, for example, dioxane, tetrahydrofuran or diethyl ether, or chlorinated hydrocarbons, such as, for example, dichloromethane, trichloromethane, tetrachloromethane, 1,2-dichloroethane or trichloroethylene, or hydrocarbons, such as benzene, xylene, toluene, hexane, cyclohexane, or petroleum fractions, or nitromethane, dimethylformamide, acetonitrile, acetone or hexamethylphosphoric triamide. It is likewise possible to employ mixtures of the solvents mentioned.

Suitable bases are inorganic or organic bases. These preferably include alkali metal hydroxides, such as, for example, sodium hydroxide or potassium hydroxide, or alkaline-earth metal hydroxides, such as barium hydroxide, or alkali metal carbonates, such as, for example, sodium carbonate or potassium carbonate, or alkaline-earth metal carbonates, such as calcium carbonate, or organic amines, such as, for example, triethylamine, pyridine, methylpiperidine, piperidine or morpholine.

It is also possible to employ as bases alkali metals, such as sodium, or the hydrides thereof, such as sodium hydride.

The process is generally carried out in a temperature range from 0° C. to +150° C., preferably from +10° C. to +100° C.

The process is generally carried out at atmospheric pressure. However, it is also possible to carry out the process at subatmospheric pressure or superatmospheric pressure (for example in a range from 0.5 to 5 bar).

In general, 0.5 to 5, preferably 1 to 2 moles of halide are employed relative to 1 mole of nitrophenyl compound. The base is generally employed in an amount from 0.5 to 5 moles, preferably from 1 to 3 moles, relative to the halide.

Examples of nitrophenyl compounds used according to the invention are:
2-nitrophenol,
3-nitrophenol,
4-nitrophenol.

Examples of halides used according to the invention are:
8-chloromethyl-quinoline,
7-chloromethyl-quinoline,
2-chloromethyl-quinoline
2-chloromethyl-pyridine,
3-chloromethyl-pyridine,
4-chloromethyl-pyridine,
2-chloromethyl-4-methyl-quinoline,
8-chloromethyl-6-methyl-quinoline.

The starting compounds (VII) and (VIII) are known.

The compounds of the general formula (IVc) are prepared by

Reacting compounds of the general formula (IX)

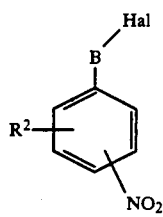

in which
R² and B have the abovementioned meaning and
Hal represents chlorine, bromine or iodine,
with compounds of the general formula (X)

H—A—R¹      (X)

in which
A and R¹ have the abovementioned meaning,
in suitable solvents, if appropriate in the presence of a base.

The process may be illustrated, for example, by the following equation:

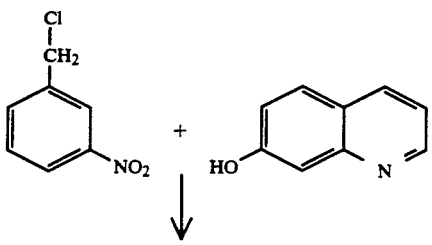

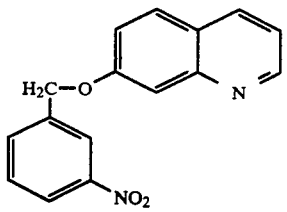

Solvents, bases and conditions for carrying out the process for preparation of the compounds of the general formula (IVc) have already been described in detail for the process for the preparation of the compounds of the general formula (IVb).

Examples of halides used according to the invention are:
2-chloromethyl-nitrophenol,
3-chloromethyl-nitrophenol,
4-chloromethyl-nitrophenol.

Examples of hydroxyl compounds which were used according to the invention are:
2-hydroxy-quinoline,
3-hydroxy-quinoline,
5-hydroxy-quinoline,
6-hydroxy-quinoline,
8-hydroxy-quinoline,
2-hydroxy-pyridine,
3-hydroxy-pyridine,
4-hydroxy-pyridine,
5-hydroxy-4-methyl-quinoline,
8-hydroxy-4-methyl-quinoline.

The compounds of the general formula (IX) and (X) used as starting materials are known.

The substituted phenylsulphonamides according to the invention can be employed as active compounds in medicaments when admixed with a pharmaceutically acceptable carrier. The new substances act as inhibitors (stimulators) of enzymatic reactions in the context of arachidonic acid metabolism, in particular of lipoxygenase. In addition, they have a thrombocyte aggregation-inhibiting effect.

They are thus preferably suitable for the treatment and prevention of disorders of the respiratory tract, such as allergies/asthma, bronchitis, emphysema, shock lung, pulmonary hypertonia, inflammations, rheumatism, oedema, thromboses, thromboembolisms, ischaemia (disturbed peripheral, cardial or cerebral circulation), cardiac and cerebral infarctions, cardiac rhythm disturbances, angina pectoris, arteriosclerosis, in tissue transplants, dermatoses, such as psoriasis, metastases, and for cytoprotection in the gastrointestinal tract.

The new active compounds can be converted into the conventional formulations, such as tablets, coated tablets, pills, granules, aerosols, syrups, emulsions, suspensions and solutions, in a known fashion using inert, non-toxic, pharmaceutically suitable excipients or solvents. In these formulations, the therapeutically active compound should in each case be present in a concentration from about 0.5 to 90% by weight of the total mixture, that is to say in amounts which are sufficient to achieve the abovementioned dosage range.

The formulations are prepared, for example, by extending the active compounds with solvents and/or excipients, if appropriate using emulsifiers and/or dispersing agents, and, for example when using water as a diluent, organic solvents can optionally be used as auxiliary solvents.

Examples of auxiliary substances which may be mentioned are: water, nontoxic organic solvents, such as paraffins (for example petroleum fractions), vegetable oils (for example groundnut/sesame oil), alcohols (for example: ethyl alcohol and glycerol), excipients, such as, for example, ground natural minerals (for example kaolins, clays, talc, chalk), group synthetic minerals (for example highly disperse silicic acid and silicates), sugars, (for example cane sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinyl pyrrolidone) and lubricants (for example magnesium stearate, talc, stearic acid and sodium lauryl sulphate).

Administration is effected in a conventional fashion, preferably orally or parenterally, in particular perlingually or intravenously. In the case of oral administration, tablets can, of course, also contain, in addition to the excipients mentioned, additives such as sodium citrate, calcium carbonate and dicalcium phosphate, together with various additional substances, such as starch, preferably potato starch, gelatin and the like. Furthermore, lubricants, such as magnesium stearate, sodium (lauryl sulphate and talc, can be co-used for tabletting. In the case of aqueous suspensions, various flavor-improving agents or colorants can be added to the active compounds in addition to the abovementioned auxiliary substances.

In the case of parenteral administration, solutions of the active compounds can be employed along with suitable liquid excipient materials.

In general, it has proven advantageous, in the case of intravenous administration, to administer amounts from about 0.001 to 1 mg/kg, preferably about 0.01 to 0.5 mg/kg of body weight in order to achieve effective results, and in the case of oral administration, the dosage is about 0.01 to 20 mg/kg, preferably 0.1 to 10 mg/kg of body weight.

Nevertheless, it may at times be necessary to deviate from the amounts mentioned, and in particular to do so as a function of the body weight, the type of administration, the individual behavior towards the medicament, the nature of the formulation of the medicament, and the time or interval over which administration takes place. Thus, it may in some cases be sufficient to manage with less than the abovementioned minimum amount, whilst in other cases the upper limit mentioned must be exceeded. Where relatively large amounts are administered, it may be advisable to divide these into several individual administrations over the course of the day.

The substituted phenylsulphonamides according to the invention can be employed both in human medicine and in veterinary medicine.

PREPARATION EXAMPLES

The retention times $R_t$ (min) are determined using a HPLC instrument (Knauer) on Hibar columns (Merck).
System a: RP-8, 7 μm.
Flow rate: 2 ml/min.
Eluent: acetonitrile/water: 70:30 (v/v).

EXAMPLE 1

8-(2-nitrophenoxy)quinoline

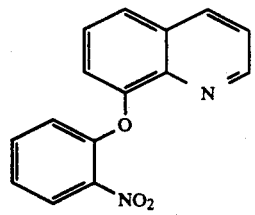

29 g of 8-hydroxyquinoline and 28 g of anhydrous potassium carbonate are stirred at 25° C. for 1 hour in 400 ml of dimethylformamide. 21 ml of 2-fluoro-nitrobenzene, dissolved in 100 ml of dimethylformamide, are added dropwise, and the reaction mixture is stirred at 25° C. for 15 hours. The solvent is removed by evaporation in vacuo, and the residue is taken up in ethyl acetate and washed three times with water. After drying over sodium sulphate, the solvent is removed by evaporating in vacuo, and the residue is recrystallized from methanol.
Yield: 82% of theory.
Melting point: 113°-114° C. (methanol).
The following were prepared analogously to Example 1:

EXAMPLE 2

8-(4-nitrophenoxy)quinoline

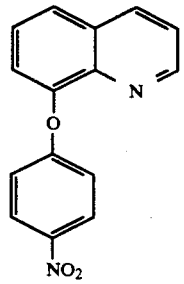

Yield: 80%.
Melting point: 165°-166° C. (methanol).

EXAMPLE 3

8-(3-nitrophenoxy)quinoline

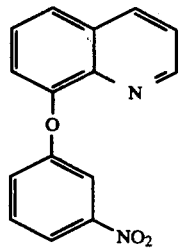

Yield: 58% of theory.
Melting point: 133°-134° C. (methanol).

EXAMPLE 4

4-methyl-8-(4-nitrophenoxy)quinoline

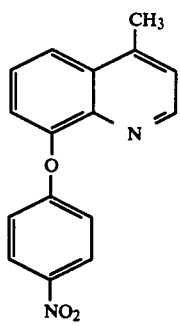

Yield: 88% of theory.

Melting point: 148°-149° C. (methanol).

EXAMPLE 5

8-(2-chloro-4-nitrophenoxy)quinoline

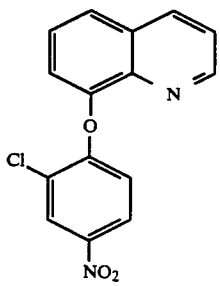

Yield: 89% of theory.

Melting point: 113°-115° C. (ethanol).

EXAMPLE 6

6-methyl-8-(4-nitrophenoxy)quinoline

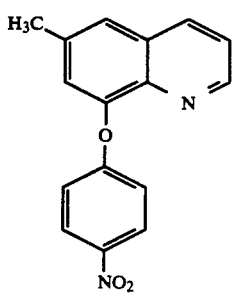

Yield: 60% of theory.

Melting point: 143° C. (ethanol).

EXAMPLE 7

4-methyl-8-(2-nitrophenoxy)quinoline

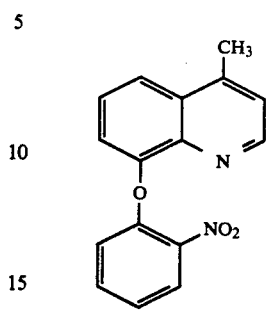

Yield: 69% of theory.

Melting point: 98°-99° C. (ethanol/water).

EXAMPLE 8

6-(2-nitrophenoxy)quinoline

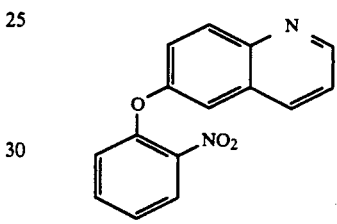

Yield: 86% of theory.

Melting point: 114°-116° C. (ethanol).

EXAMPLE 9

2-(4-nitrophenoxymethyl)quinoline

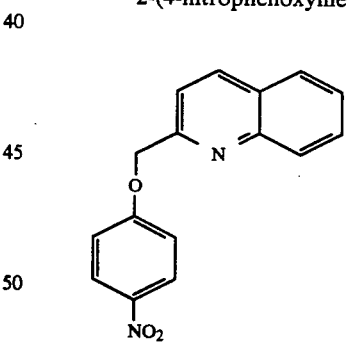

28 g of 4-nitrophenol and 55 g of anhydrous potassium carbonate are stirred for 1 hour at 25° C. in 300 ml of dimethylformamide. After dropwise addition of a suspension of 43 g of 2-chlorophenyl-quinoline hydrochloride in 100 ml of dimethylformamide, the mixture is stirred for 15 hours at 40°-50° C. After removal of the solvent by evaporation, the residue is stirred with water, filtered off under suction and recrystallized from methanol.

Yield: 91% of theory.

Melting point: 144°-145° C. (methanol).

The following were prepared analogously to Example 9:

EXAMPLE 10

2-(2-nitrophenoxymethyl)quinoline

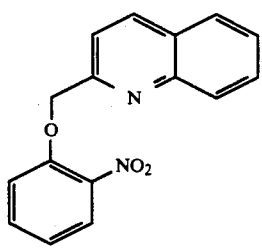

Yield: 83% of theory.

Melting point: 121°-122° C. (methanol).

EXAMPLE 11

2-(3-nitrophenoxymethyl)quinoline

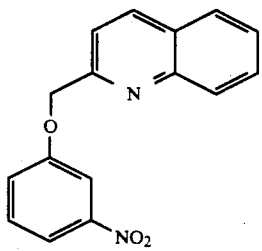

Yield: 94% of theory.

Melting point: 109° C. (methanol).

EXAMPLE 12

2-(2-cyano-4-nitrophenoxymethyl)quinoline

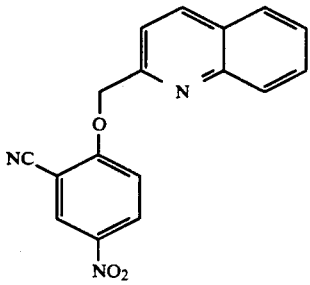

Yield: 50% of theory.

Melting point: 161°-162° C. (methanol).

EXAMPLE 13

2-[1-(4-nitrophenoxy)ethyl]quinoline

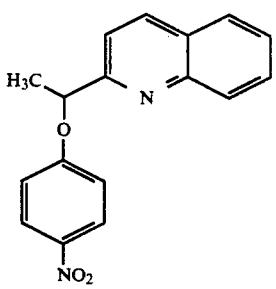

Yield: 75% of theory.
$R_f = 2.07$ (system a).

EXAMPLE 14

2-(2-ethoxycarbonyl-4-nitrophenoxymethyl)quinoline

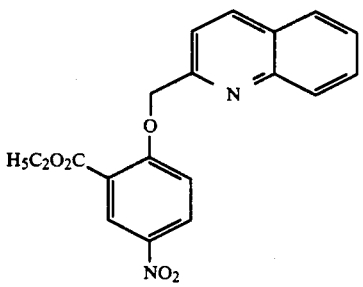

Yield: 40% of theory.
Melting point: 139°-140° C. (ethanol).

EXAMPLE 15

8-(2-nitrobenzyloxy)quinoline

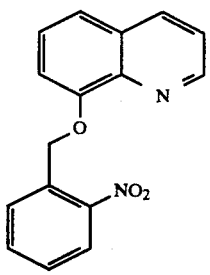

42 g of 8-hydroxyquinoline and 40 g of anhydrous potassium carbonate are stirred for 1 hour at 25° C. in 400 ml of dimethylformamide. 50 g of 2-nitrobenzyl chloride in 150 ml of dimethylformamide are then added dropwise, and the mixture is stirred for 15 hours at 25° C. and evaporated. The residue is stirred with water, filtered off under suction and recrystallized from ethanol.

Yield: 84% of theory.
Melting point: 151°-153° C. (ethanol).

The following were prepared analogously to Example 15:

EXAMPLE 16

8-(3-nitrobenzyloxy)quinoline

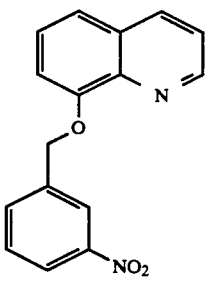

Yield: 70% of theory.
Melting point: 98°-99° C. (ethanol).

EXAMPLE 17

2-[N-methyl-N-(3-nitrobenzyl)aminoethyl]pyridine

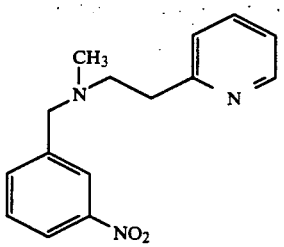

6.8 g of 3-nitrobenzyl chloride in 25 ml of methanol are slowly added dropwise to a solution of 5.4 g of 2-(2-methylaminoethyl)pyridine in 20 ml of methanol at 40° C. 15 ml of triethylamine in 15 ml of methanol are subsequently added, and the mixture is stirred for 15 hours at 40° C. After removal of the solvent by evaporation in vacuo, the residue is taken up in 300 ml of water and extracted three times with dichloromethane. After drying over sodium sulphate, the dichloromethane is evaporated in vacuo and the residue is chromatographed on silica gel (eluent: dichloromethane/methanol 100:5).

Yield: 82% of theory.
Boiling point: 245° C./0.5 mm (bulb tube).

EXAMPLE 18

2-[N-(3-nitrobenzyl)-N-methyl]aminopyridine

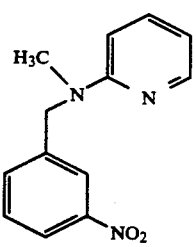

21.6 g of 2-methylaminopyridine and 34.2 g of 3-nitrobenzyl chloride are warmed at 50° C. for 30 minutes. After adding 3 g of dimethylaminopyridine, the mixture is warmed at 100° C. for 3 hours. After cooling, the reaction mixture is taken up in dichloromethane and washed with 2N NaOH and water, dried over sodium sulphate and concentrated. The residue is chromatographed through silica gel (eluent: dichloromethane). The product crystallizes out.

Yield: 55% of theory.
Melting point: 56°-57° C.

EXAMPLE 19

8-(2-aminophenoxy)quinoline

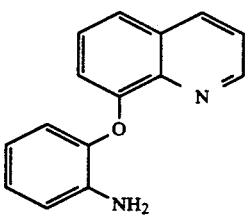

35.4 g of 8-(2-nitrophenoxy)quinoline and 3.4 g of 10% palladium/charcoal are suspended in 350 ml of methanol under nitrogen and warmed. Under reflux, 27.8 ml of hydrazine hydrate are slowly added dropwise, and the mixture is then refluxed for a further 2 hours. After cooling, the catalyst is filtered off under suction and the solvent is removed by evaporation in vacuo. The residue is recrystallized from methanol.

Yield: 69% of theory.
Melting point: 135° C. (methanol).

The following were prepared analogously to Example 19:

EXAMPLE 20

7-(4-aminophenoxy)quinoline

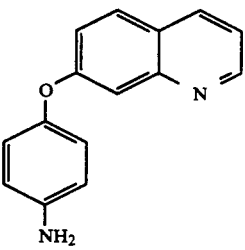

Yield: 72% of theory.
Melting point: 131° C. (ethanol).

EXAMPLE 21

8-(4-aminophenoxy)quinoline

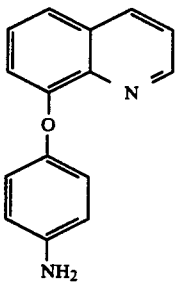

Yield: 68% of theory.
Melting point: 204° C. (methanol).

EXAMPLE 22

8-(3-aminophenoxy)quinoline

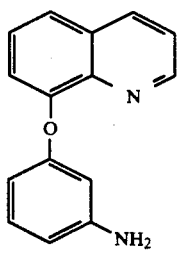

Yield: 22% of theory.

Melting point: 98°–100° C. (methanol).

EXAMPLE 23

8-(4-aminophenoxy)-4-methyl-quinoline

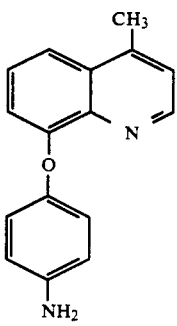

Yield: 71% of theory.

Melting point: 157°–159° C. (ethanol).

EXAMPLE 24

8-(4-amino-2-chlorophenoxy)quinoline

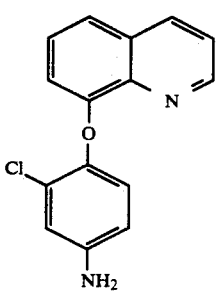

Yield: 28% of theory.

Melting point: 181°–182° C.

EXAMPLE 25

8-(4-aminophenoxy)-6-methyl-quinoline

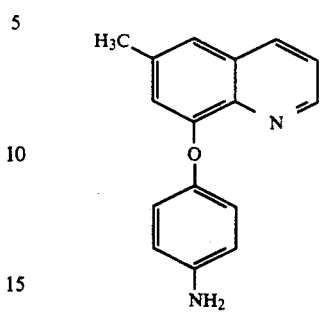

Yield: 77% of theory.
Melting point: 184°–185° C. (ethanol).

EXAMPLE 26

8-(2-aminophenoxy)-4-methyl-quinoline

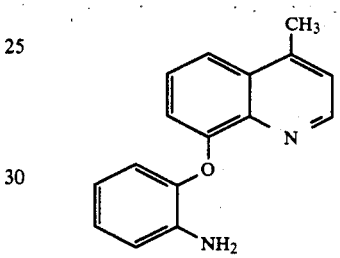

Yield: 84% of theory.
Melting point: 160°–161° C. (ethanol).

EXAMPLE 27

6-(2-aminophenoxy)quinoline

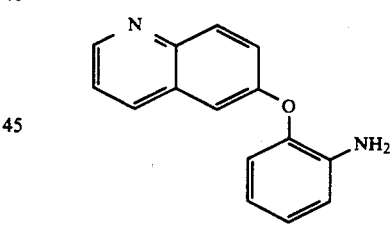

Yield: 74% of theory.
Melting point: 115°–117° C. (ethanol).

EXAMPLE 28

2-(4-aminophenoxymethyl)quinoline

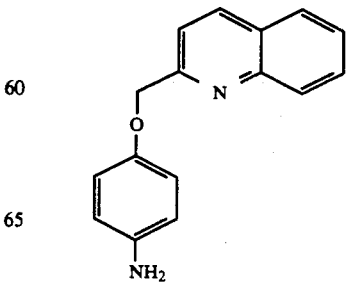

Yield: 64% of theory.

Melting point: 126°-128° C. (methanol).

EXAMPLE 29

2-(2-aminophenoxymethyl)quinoline

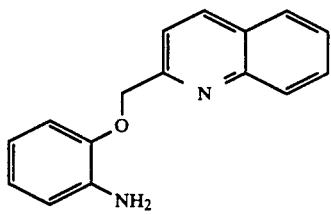

Yield: 71% of theory.

Melting point: 66°-69° C. (i-propanol).

EXAMPLE 30

2-(3-aminophenoxymethyl)quinoline

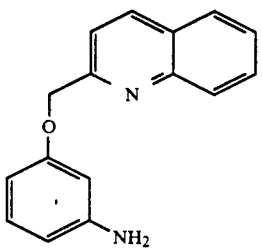

Yield: 67% of theory.

Melting point: 98°-99° C. (methanol).

EXAMPLE 31

2-(4-amino-2-cyano-phenoxymethyl)quinoline

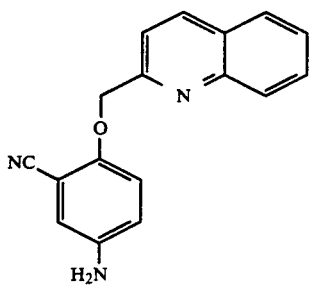

Yield: 49% of theory.

Melting point: 156° C.

EXAMPLE 32

2-[1-(4-aminophenoxy)ethyl]quinoline

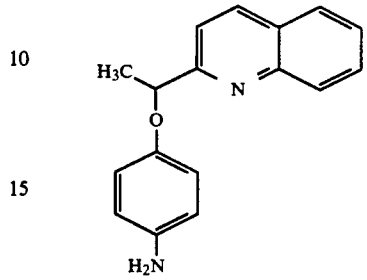

Yield: 95% of theory.

Melting point: 86°-88° C.

EXAMPLE 33

2-(4-amino-2-ethoxycarbonyl--phenoxymethyl)quinoline

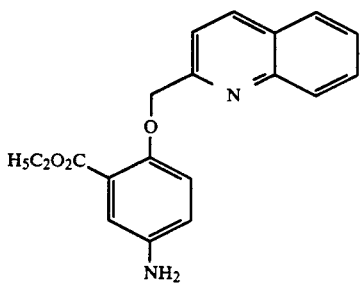

Yield: 57% of theory.

Melting point: 93°-95° C.

EXAMPLE 34

8-(2-aminobenzyloxy)quinoline

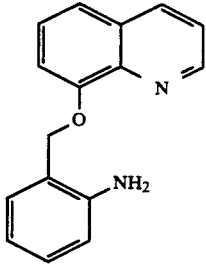

Yield: 60% of theory.

Melting point: 103°-105° C. (ethyl acetate).

EXAMPLE 35

8-(3-aminobenzyloxy)quinoline

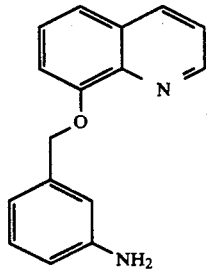

Yield: 74% of theory.

Melting point: 146°–147° C. (ethanol).

EXAMPLE 36

2-[N-(3-aminobenzyl)-N-methyl]aminopyridine

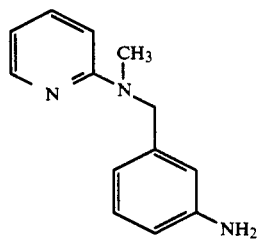

Yield: 92% of theory.

$R_t = 1.64$ (System a).

EXAMPLE 37

2-[2-(N-3-aminobenzyl-N-methyl)aminoethyl]pyridine

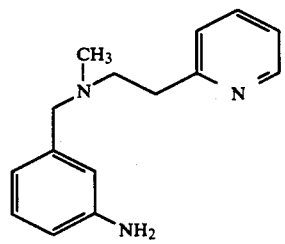

Yield: 64% of theory.

$R_f = 0.26$ (CH$_2$Cl$_2$/CH$_3$OH 10:1).

EXAMPLE 38

N-[2-(quinolin-8-yloxy)phenyl]-4-chlorobenzenesulphonamide

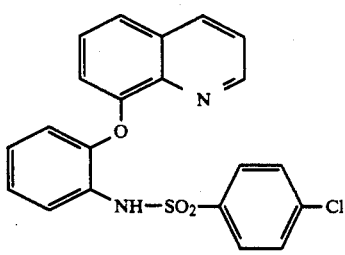

3.54 g of 8-(2-aminophenoxy)quinoline are dissolved in 70 ml of dichloromethane, and a solution of 3.17 g of 4-chlorobenzenesulphonyl chloride in 30 ml of dichloromethane is added at 25° C. After 1 hour, 2.42 ml of pyridine are added, and the mixture is stirred for 15 hours at 25° C. After removal of the solvent by evaporation, the residue is stirred with water. The product is filtered off and recrystallized from ethanol.

Yield: 94% of theory.

Melting point: 135°–137° C. (ethanol).

The following were prepared analogously to Example 38:

EXAMPLE 39

N-[2-(quinolin-8-yloxy)phenyl]-3-trifluoromethylbenzenesulphonamide

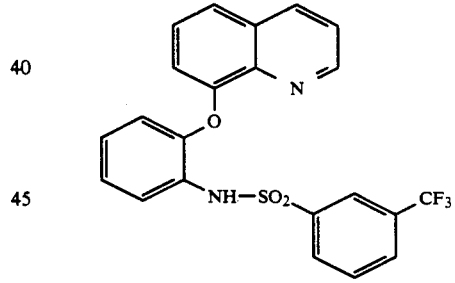

Yield: 68% of theory.

$R_t = 2.89$ (system a).

EXAMPLE 40

N-[2-(quinolin-8-yloxy)phenyl]butanesulphonamide

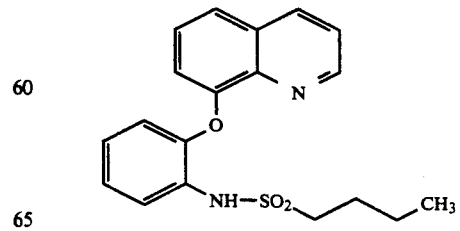

Yield: 51% of theory.

Melting point: 87°–88° C.

EXAMPLE 41

N-[2-(quinolin-8-yloxy)phenyl]-3-chloropropanesulphonamide

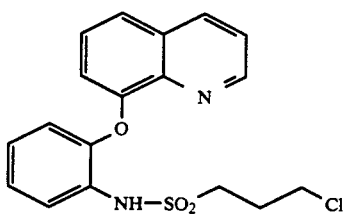

Yield: 50% of theory.

$R_f$ = 2.00 (system a).

EXAMPLE 42

N-[2-(quinolin-8-yloxy)phenyl]-4-fluorobenzenesulphonamide

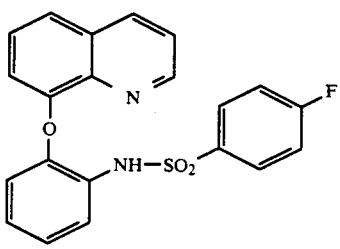

Yield: 46% of theory.

Melting point: 243°–244° C. (methanol).

EXAMPLE 43

N-[4-(quinolin-8-yloxy)phenyl]-4-chlorobenzenesulphonamide

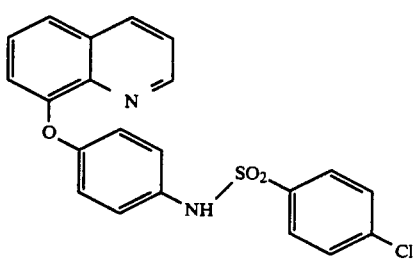

Yield: 91% of theory.

Melting point: 220° C. (methanol).

EXAMPLE 44

N-[4-(quinolin-8-yloxy)phenyl]-3-trifluoromethylbenzenesulphonamide

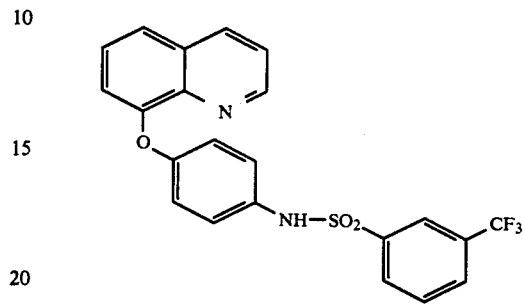

Yield: 66% of theory.

Melting point: 186° C. (methanol).

EXAMPLE 45

N-[4-(quinolin-8-yloxy)phenyl]butanesulphonamide

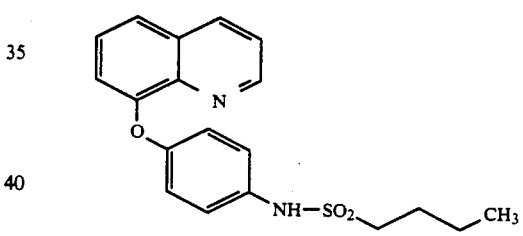

Yield: 65% of theory.

Melting point: 162° C. (methanol).

EXAMPLE 46

N-[4-(quinolin-8-yloxy)phenyl]-3-chloropropanesulphonamide

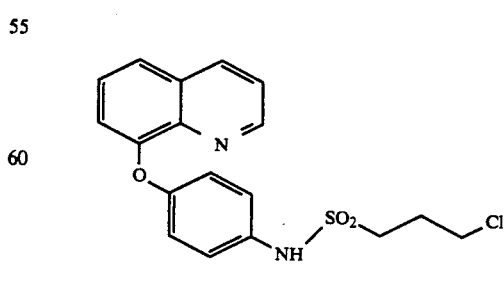

Yield: 69% of theory.

Melting point: 161°–162° C. (methanol).

EXAMPLE 47

N-[4-(quinolin-8-yloxy)phenyl]-4-fluorobenzenesulphonamide

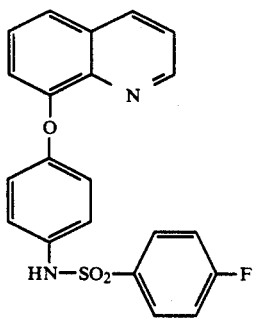

Yield: 76% of theory.
Melting point: 181°-183° C. (methanol).

EXAMPLE 48

N-[3-(quinolin-8-yloxy)phenyl]-4-chlorobenzenesulphonamide

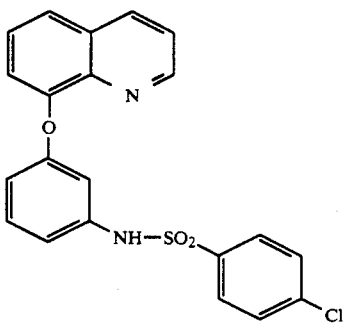

Yield: 61% of theory.
Melting point: 190°-191° C. (ethanol).

EXAMPLE 49

N-[3-(quinolin-8-yloxy)phenyl]-3-trifluoromethylbenzenesulphonamide

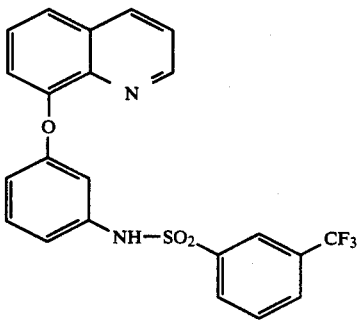

Yield: 53% of theory.
Melting point: 171°-173° C. (ethanol).

EXAMPLE 50

N-[3-(quinolin-8-yloxy)phenyl]-4-fluorobenzenesulphonamide

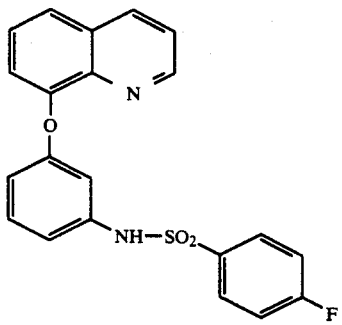

Yield: 51% of theory.
Melting point: 201°-202° C. (methanol).

EXAMPLE 51

N-[3-(quinolin-8-yloxy)phenyl]-3-chloropropanesulphonamide

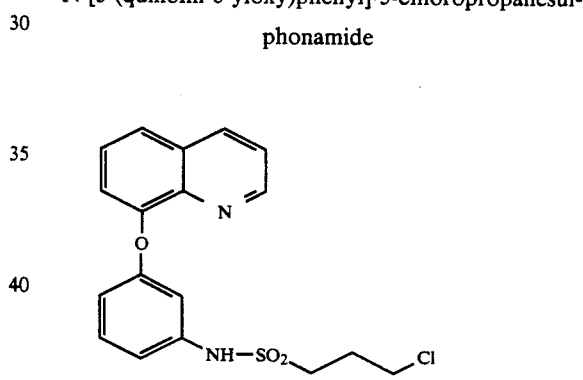

Yield: 66% of theory.
Melting point: 138°-140° C. (ethanol).

EXAMPLE 52

N-[3-(quinolin-8-yloxy)phenyl]butanesulphonamide

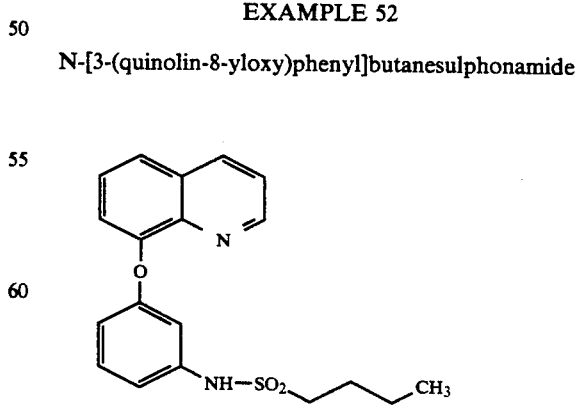

Yield: 56% of theory.
Melting point: 107°-108° C. (diisopropyl ether).

EXAMPLE 53

N-[4-(quinolin-7-yloxy)phenyl]-4-chlorobenzenesulphonamide

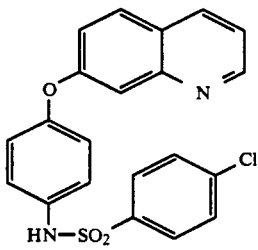

Yield: 93% of theory.

Melting point: 208° C. (methanol).

EXAMPLE 54

N-[4-(quinolin-7-yloxy)phenyl]-3-trifluoromethylbenzenesulphonamide

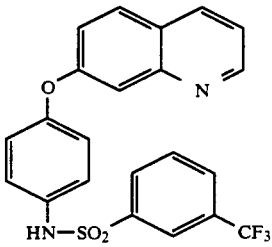

Yield: 64% of theory.

Melting point: 190° C. (methanol).

EXAMPLE 55

N-[4-(quinolin-7-yloxy)phenyl]butanesulphonamide

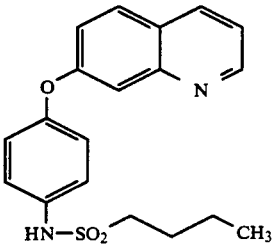

Yield: 70% of theory.

Melting point: 168° C. (methanol).

EXAMPLE 56

N-[-(quinolin-7-yloxy)phenyl]-3-chloropropanesulphonamide

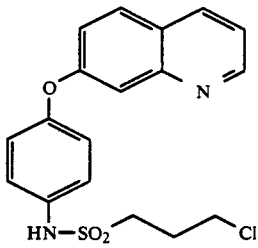

Yield: 75% of theory.

Melting point: 175°-176° C. (methanol).

EXAMPLE 57

N-[4-(quinolin-7-yloxy)phenyl]-4-fluorobenzenesulphonamide

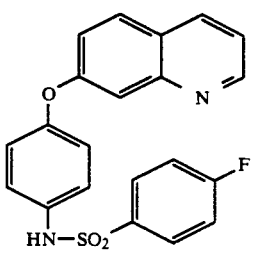

Yield: 61% of theory.

Melting point: 175°-178° C. (methanol).

EXAMPLE 58

N-[4-(4-methylquinolin-8-yloxy)phenyl]-4-chlorobenzenesulphonamide

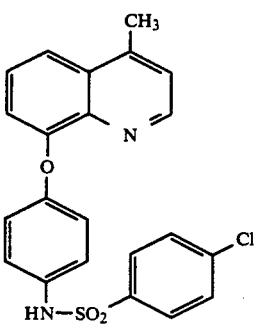

Yield: 94% of theory.

Melting point: 223°-224° C. (methanol).

EXAMPLE 59

N-[4-(4-methylquinolin-8-yloxy)phenyl]-3-trifluoromethylbenzenesulphonamide

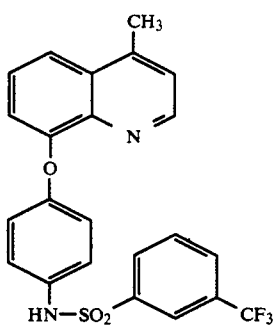

Yield: 70% of theory.
Melting point: 202°-203° C.

EXAMPLE 60

N-[4-(4-methylquinolin-8-yloxy)phenyl]butanesulphonamide

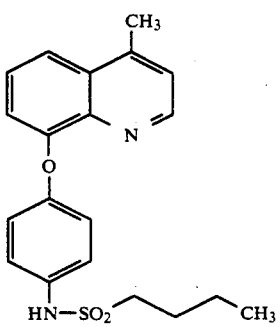

Yield: 81% of theory.
Melting point: 208°-209° C. (ethanol).

EXAMPLE 61

N-[4-(quinolin-8-yloxy)-3-chlorophenyl]-4-chlorobenzenesulphonamide

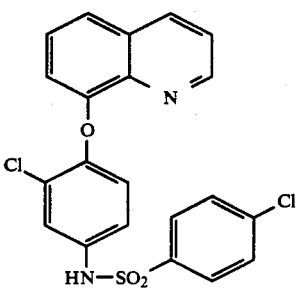

Yield: 90% of theory.
Melting point: 198°-198° C. (ethanol).

EXAMPLE 62

N-[4-(quinolin-8-yloxy)-3-chlorophenyl]-3-trifluoromethylbenzenesulphonamide

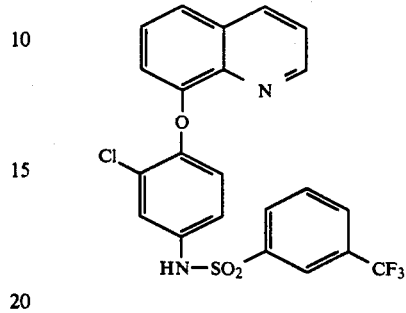

Yield: 88% of theory.
Melting point: >245° C. (methanol).

EXAMPLE 63

N-[4-(6-methylquinolin-8-yloxy)phenyl]butanesulphonamide

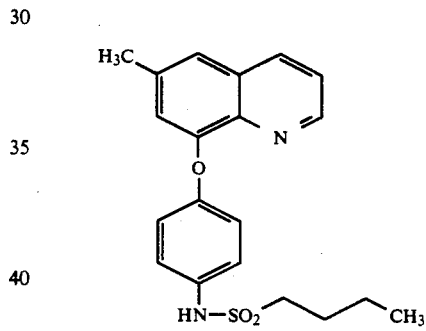

Yield: 88% of theory.
Melting point: 189°-190° C. (ethanol).

EXAMPLE 64

N-[4-(6-methylquinolin-8-yloxy)phenyl]-4-chlorobenzenesulphonamide

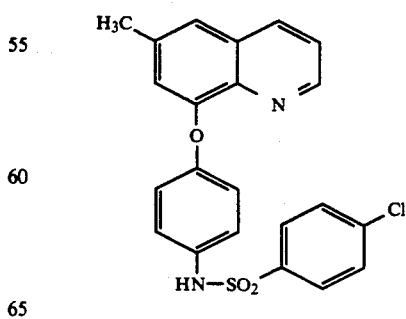

Yield: 94% of theory.
Melting point: >245° C.

EXAMPLE 65

N-[2-(4-methylquinolin-8-yloxy)phenyl]-4-chlorobenzenesulphonamide

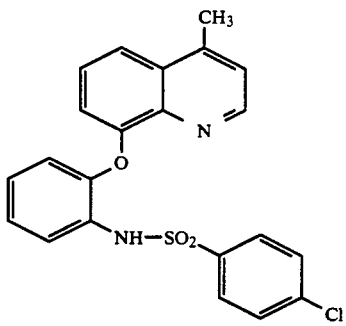

Yield: 80% of theory.
Melting point: 123°–125° C. (methanol).

EXAMPLE 66

N-[2-(4-methylquinolin-8-yloxy)phenyl]-butanesulphonamide

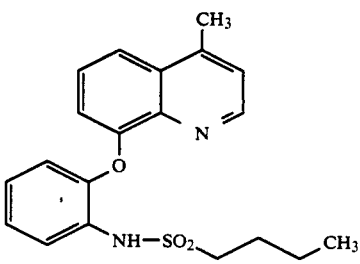

Yield: 62% of theory.
$R_f = 2.21$ (system a).

EXAMPLE 67

N-[4-(quinolin-6-yloxy)phenyl]-4-chlorobenzenesulphonamide

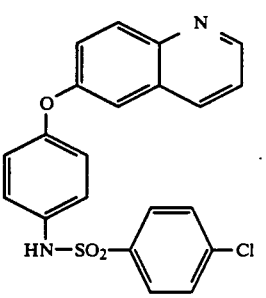

Yield: 33% of theory.
Melting point: >255° C.

EXAMPLE 68

N-[4-(quinolin-6-yloxy)phenyl]-3-trifluoromethylbenzenesulphonamide

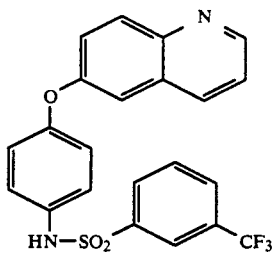

Yield: 60% of theory.
Melting point: 142°–143° C. (methanol).

EXAMPLE 69

N-[4-(quinolin-6-yloxy)phenyl]butanesulphonamide

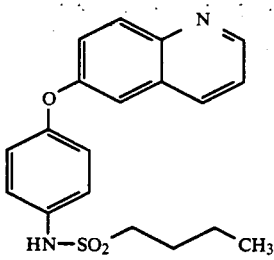

Yield: 84% of theory.
Melting point: 170° C. (methanol).

EXAMPLE 70

N-[2-(quinolin-6-yloxy)phenyl]-4-chlorobenzenesulphonamide

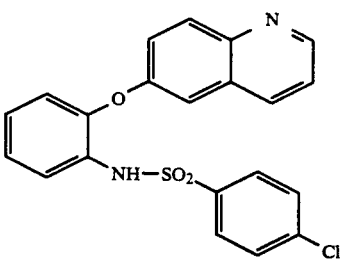

Yield: 84% of theory.
Melting point: 151°–152° C. (ethanol).

EXAMPLE 71

N-[2-(quinolin-6-yloxy)phenyl]butanesulphonamide

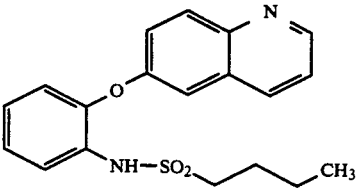

Yield: 62% of theory.

Melting point: 131°-133° C. (ethanol).

EXAMPLE 72

N-[4-(4-methylquinolin-2-yloxy)phenyl]-4-chlorobenzenesulphonamide

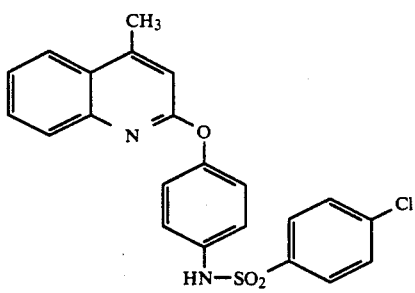

Yield: 88% of theory.
Melting point: 174°-176° C. (methanol).

EXAMPLE 73

N-[4-(quinolin-2-yl-methyloxy)phenyl]-4-chlorobenzenesulphonamide

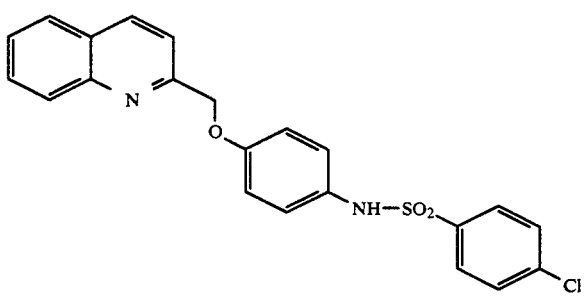

Yield: 82% of theory.
Melting point: 125° C. (methanol).

EXAMPLE 74

N-[4-(quinolin-2-yl-methyloxy)-phenyl]-3-trifluoromethylbenzenesulphonamide

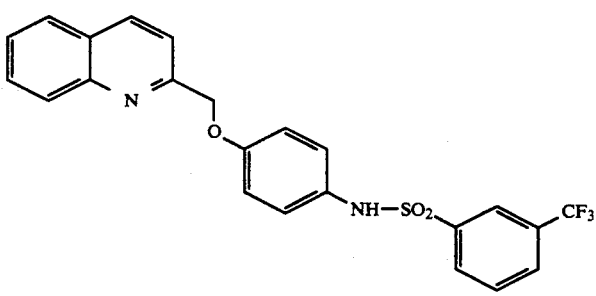

Yield: 93% of theory.
Melting point: 81°-83° C. (methanol).

EXAMPLE 75

N-[4-(quinolin-2-yl-methyloxy)phenyl]butanesulphonamide

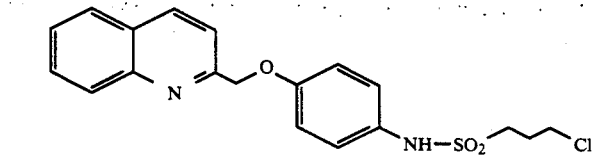

Yield: 77% of theory
Melting point: 113° C. (ethanol)

EXAMPLE 76

N-[4-(quinolin-2-yl-methyloxy)phenyl]-3-chloropropanesulphonamide

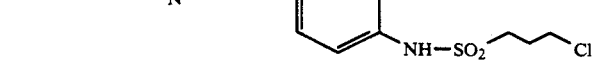

Yield: 74% of theory.

Melting point: 117° C. (methanol).

EXAMPLE 77

N-[4-(quinolin-2-yl-methyloxy)phenyl]pentafluorobenzenesulphonamide

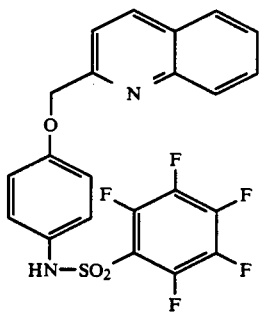

Yield: 37% of theory.

Melting point: 170°-178° C. (toluene).

EXAMPLE 78

N-[4-(quinolin-2-yl-methyloxy)phenyl]-1-methylbutanesulphonamide

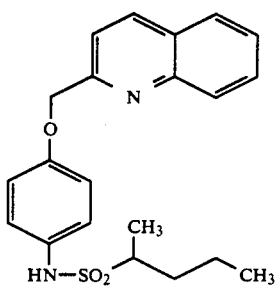

Yield: 70% of theory.

$R_5 = 1.68$ (system a).

EXAMPLE 79

N-[2-(quinolin-2-yl-methyloxy)phenyl]-4-chlorobenzenesulphonamide

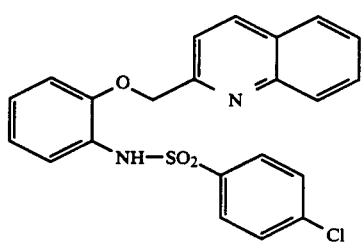

Yield: 82% of theory.
Melting point: 129°-130° C. (methanol).

EXAMPLE 80

N-[2-(quinolin-2-yl-methyloxy)phenyl]-3-trifluoromethylbenzenesulphonamide

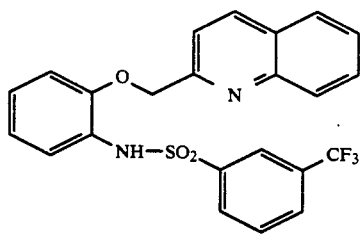

Yield: 79% of theory.
Melting point: 154°-155° C. (methanol).

EXAMPLE 81

N-[2-(quinolin-2-ylmethyloxy)phenyl]butanesulphonamide

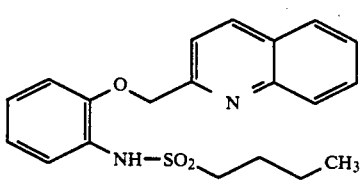

Yield: 40% of theory.
Melting point: 93°-94° C. (methanol).

EXAMPLE 82

N-[2-(quinolin-2-yl-methyloxy)phenyl]-3-chloropropanesulphonamide

Yield: 67% of theory.
Melting point: 100°-101° C. (methanol).

EXAMPLE 83

N-[3-(quinolin-2-yl-methyloxy)phenyl]-4-chlorobenzenesulphonamide

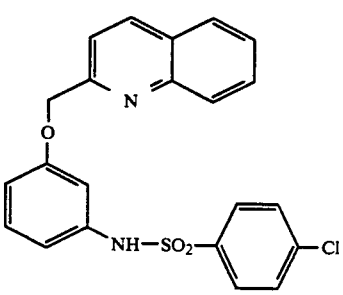

Yield: 85% of theory.
Melting point: 157°-159° C. (isopropanol).

EXAMPLE 84

N-[3-(quinolin-2-yl-methyloxy)phenyl]-3-trifluoromethylbenzenesulphonamide hydrochloride

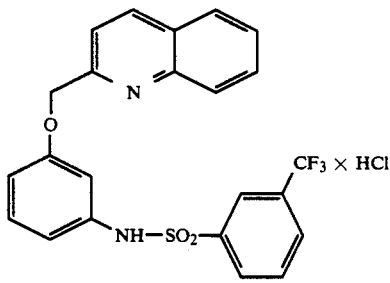

Yield: 81% of theory.
Melting point: 183°-187° C. (isopropanol).

EXAMPLE 85

N-[3-(quinolin-2-yl-methyloxy)phenyl]butanesulphonamide

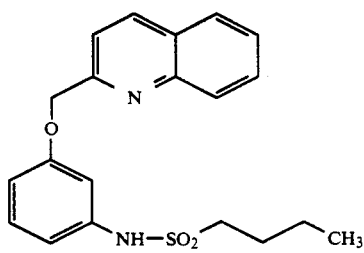

Yield: 67% of theory.
Melting point: 105°-106° C. (isopropanol).

EXAMPLE 86

N-[3-(quinolin-2-yl-methyloxy)phenyl]-3-chloropropanesulphonamide

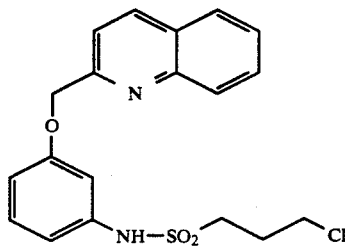

Yield: 90% of theory.
Melting point: 116°-117° C. (isopropanol).

EXAMPLE 87

N-{4-[1-(quinolin-2-yl)ethyloxy]phenyl}butanesulphonamide

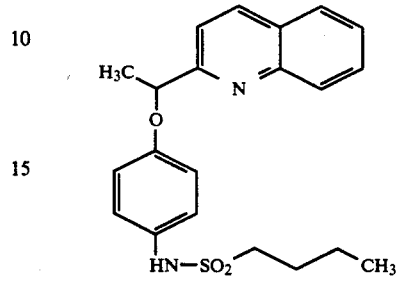

Yield: 89% of theory.
$R_f = 1.80$ (System a).

EXAMPLE 88

N-[4-(quinolin-2-yl]methyloxy-3-cyano-phenyl]-butanesulphonamide

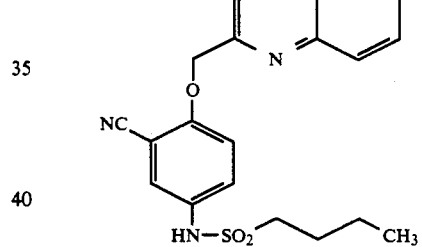

Yield: 43% of theory.
Melting point: 158°-160° C. (isopropanol).

EXAMPLE 89

N-[3-ethoxycarbonyl-4-(quinolin-2-yl)methyloxyphenyl]-butanesulphonamide

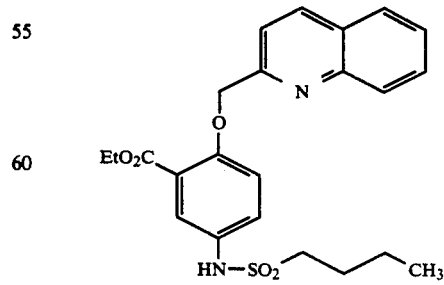

Yield: 33% of theory.
Melting point: 90°-90° C.

EXAMPLE 90

N-[2-(quinolin-8-yloxymethyl)phenyl]-4-chlorobenzenesulphonamide

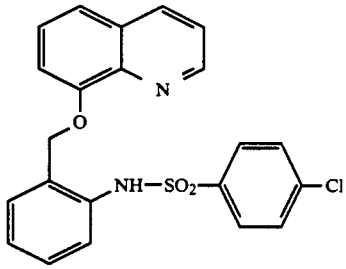

Yield: 31% of theory.
Melting point: 136°-137° C.

EXAMPLE 91

N-[3-(quinolin-8-yloxymethyl)phenyl]-4-chlorobenzenesulphonamide

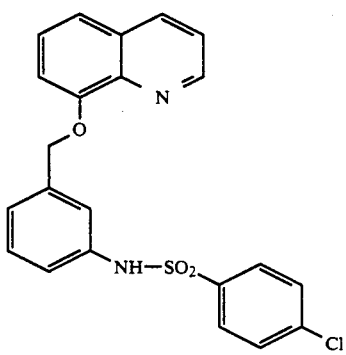

Yield: 81% of theory.
Melting point: 201°-202° C. (methanol).

EXAMPLE 92

N-[3-(quinolin-8-yloxymethyl)phenyl]-3-trifluoromethylbenzenesulphonamide

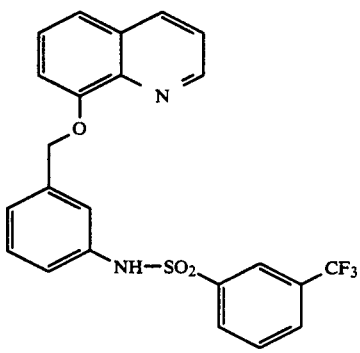

Yield: 60% of theory.
Melting point: 210°-212° C. (ethanol).

EXAMPLE 93

N-[3-(quinolin-8-yloxymethyl)phenyl]butanesulphonamide

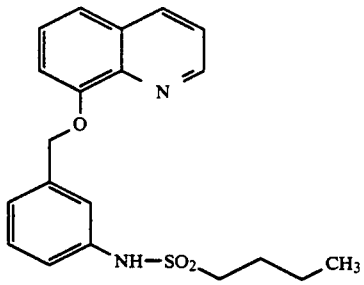

Yield: 42% of theory.
Melting point: 136°-137° C. (ethanol).

EXAMPLE 94

N-[3-(quinolin-8-yloxymethyl)phenyl)-4-fluorobenzenesulphonamide

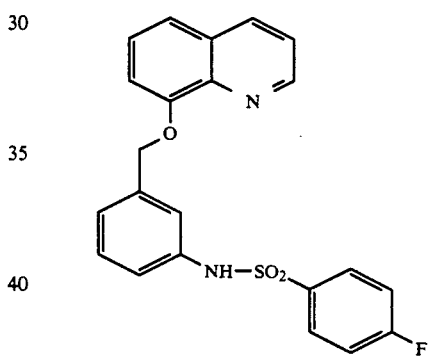

Yield: 88% of theory.
Melting point: 206°-207° C. (ethanol).

EXAMPLE 95

N-[2-(quinolin-8-yloxymethyl)phenyl]butanesulphonamide

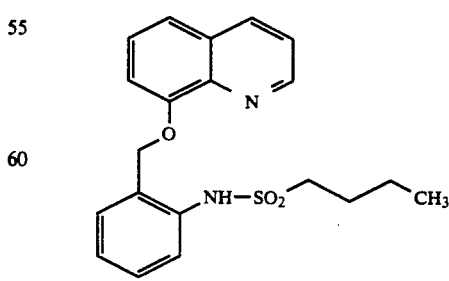

Yield: 56% of theory.
Melting point: 88°-89° C. (ethanol).

EXAMPLE 96

N-[2-(quinolin-8-yloxymethyl)phenyl]-3-trifluoromethylbenzenesulphonamide

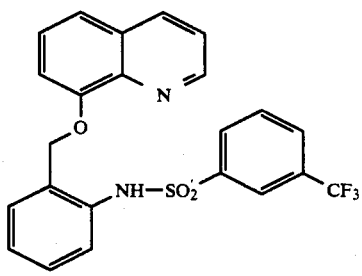

Yield: 81% of theory.

Melting point: 120°–121° (ethanol).

EXAMPLE 97

N-[2-(quinolin-8-yloxymethyl)phenyl]-3-chloropropanesulphonamide

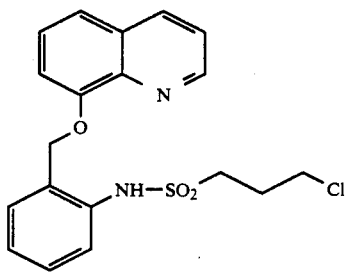

Yield: 57% of theory.

Melting point: 96°–97° C.

EXAMPLE 98

N-[3-(quinolin-8-yloxymethyl)phenyl]-3-chloropropanesulphonamide

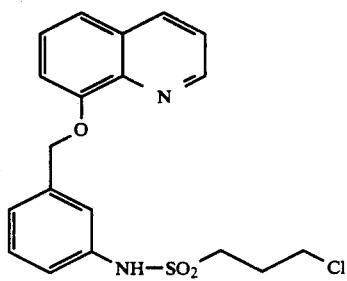

Yield: 72% of theory.

Melting point: 142°–143° C. (ethanol).

EXAMPLE 99

N-[2-(quinolin-8-yloxymethyl)phenyl]-4-fluorobenzenesulphonamide

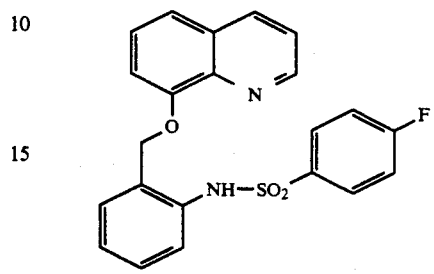

Yield: 95% of theory.

Melting point: 121°–122° C. (ethanol).

EXAMPLE 100

N,N',N'-[3-(methyl-2-pyridyl-aminomethyl)phenyl]-butanesulphonamide

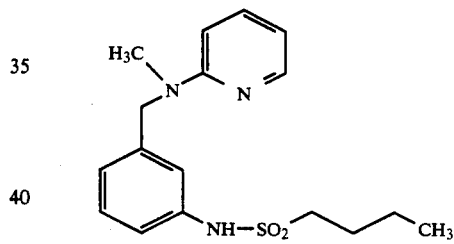

Yield: 78% of theory.

$R_f = 1.80$ (System a).

EXAMPLE 101

N,N',N'-[3-(methyl-2-pyridinyl-aminomethyl)phenyl]-3-chloropropanesulphonamide

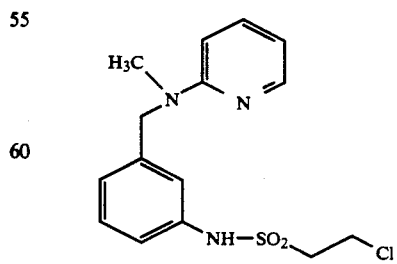

Yield: 71% of theory.

Melting point: 63°–65° C.

EXAMPLE 102

N,N',N'-[3-(methyl-2-pyridyl-aminomethyl)phenyl]-3-trifluoromethylbenezenesulphonamide

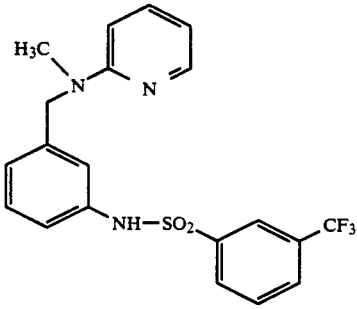

Yield: 81% of theory.
Melting point: 192°-197° C.

EXAMPLE 103

N,N',N'-[3-(methyl-2-pyridyl-aminomethyl)phenyl]-4-chlorobenzenesulphonamide

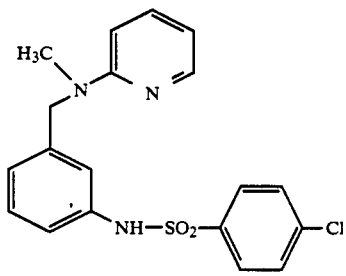

Yield: 70% of theory.
Melting point: 113°-114° C.

EXAMPLE 104

N,N',N'-{3-{[methyl-2-(2-pyridyl)ethyl]aminomethyl}-phenyl}-4-chlorobenzenesulphonamide

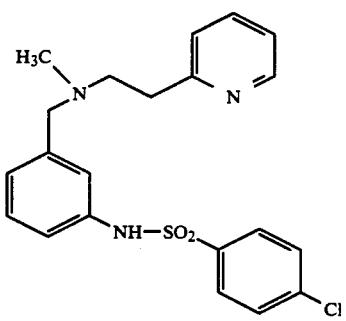

Yield: 74% of theory.
$R_f$=0.58 (CH2Cl2/CH3OH 10.1).

EXAMPLE 105

N,N',N'-{3-[methyl-2-(2-pyridyl)ethyl]aminomethyl-phenyl}-3-trifluoromethylbenzenesulphonamide

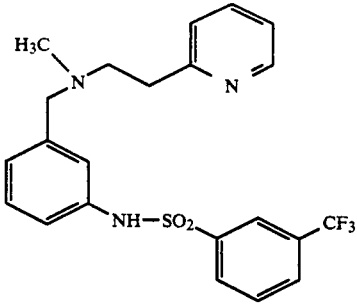

Yield: 73% of theory.
$R_f$=0.59 (CH2Cl2CH3OH 10:1).

EXAMPLE 106

N,N',N'-{3-{[methyl-2-(2-pyridyl)ethyl]aminomethyl}-phenyl}butanesulphonamide

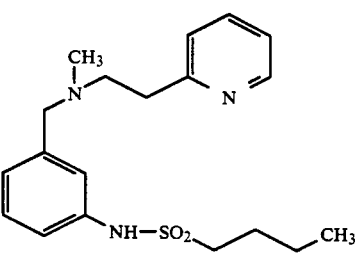

Yield: 35% of theory.
$R_f$=0.58 (CH2Cl2/CH3OH 10:1).

USE EXAMPLES

EXAMPLE 107

Inhibition of thrombotyte aggregation

In order to determine the thrombocyte aggregation-inhibiting action, blood from healthy test persons of both sexes was used. As anticoagulant, one part of 3.8% strength aqueous sodium citrate solution was mixed with 9 parts of blood. From this blood, platelet-rich citrate plasma (PRP) was obtained by centrifugation (Jürgens/Beller, Klinische Methoden der Blutgerinnungsanalyse [Clinical Methods of Blood Coagulation Analysis]; Thieme Verlag, Stuttgart, 1959).

For these investigations, 0.8 ml of PRP and 0.1 ml of the active compound solution were preincubated at 37° C. in a water bath. The thrombocyte aggregation was subsequently determined at 37° C. in an aggregometer (Therapeutische Berichte 47, 80–86, 1975) by the turbidometric method (Born, G. V. R., J. Physiol. (London), 162, 67, 1962). To this purpose, 0.1 ml of collagen, an aggregation-initiating agent, was added to the preincubated sample. The change in optical density in the PRP sample was recorded over a time period of 6 minutes, and the deflection after 6 minutes determined. For this purpose, the percentage inhibition compared to the control is calculated.

The range of the minimum effective concentration is specified as the limiting concentration (Table 1).

TABLE 1

| | Inhibition of thrombocyte aggregation |
|---|---|
| Example No. | Inhibition, μg/ml (limiting concentration) |
| 38 | 0.3–0.1 |
| 43 | 1.0–0.1 |
| 44 | 10–1 |
| 45 | 10–1 |
| 46 | 1.0–0.1 |
| 52 | 10–3 |
| 58 | 10–3 |
| 74 | 3.0–1.0 |
| 90 | 1.0–0.1 |

The liberation of leukotriene $8_4$ (LTD$_4$) in polymorphonuclear rat leukocytes (PMN) after addition of substances and calcium ionophore was determined by means of reverse phase HPLC according to Borgeat, P. et al., Proc. Nat. Acad. Sci. 76, 2148–2152 (1979) as a measure of the lipoxygenase inhibition. The in vivo activity of the compounds was determined using the mouse ear inflammation model according to Young, J. M. et al., J. of Investigative Dermatology 82, 367–371 (1984).

Examples of the values achieved according to this test by some compounds according to the invention are shown in Tables 2 and 3:

TABLE 2

| Inhibition of lipoxygenase | |
|---|---|
| Example No. | IC$_{50}$ value (g/ml) |
| 53 | $8.8 \times 10^{-8}$ |
| 54 | $1.7 \times 10^{-7}$ |
| 57 | $3.3 \times 10^{-8}$ |
| 73 | $1.0 \times 10^{-7}$ |
| 74 | $1.0 \times 10^{-7}$ |
| 75 | $5.7 \times 10^{-8}$ |
| 76 | $4.6 \times 10^{-8}$ |
| 78 | $7.4 \times 10^{-8}$ |

TABLE 3

| | Mouse ear inflammation test | |
|---|---|---|
| Example | Dose | Inhibition of inflammation, % |
| 58 | 2 mg/ear topical | 58 |
| 75 | 2 mg/ear topical | 39 |
| 78 | 2 mg/ear topical | 65 |
| 44 | 100 mg/kg per os | 38 |
| 75 | 100 mg/kg per os | 46 |
| 76 | 100 mg/kg per os | 37 |

It is noted that compounds of the present invention in which the sulphonamide group on the phenyl is attached in the 4-position to the quinoline moiety have a higher efficacy than compounds, e.g., of U.S. Pat. No. 4,675,405, in which the sulphonamide group on the phenyl is attached in the 3-position to the quinoline moiety.

It will be appreciated that the instant specification and claims are set forth by way of illustration and not limitation, and that various modifications and changes may be made without departing from the spirit and scope of the present invention.

What is claimed is:

1. A method for inhibiting lipoxygenase enzymatic reactions in a human or animal patient which comprises administering to such patient an amount effective therefor of a phenylsulphonamide of the formula

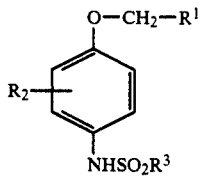

wherein
R$^1$ represents a quinolyl radical which is unsubstituted or substituted by fluoride chlorine, alkyl having up to 4 carbon atoms, alkoxy having up to 4 carbon atoms or by trifluoromethyl,
R$^2$ represents hydrogen, cyano, fluorine, chlorine, methyl, ethyl, propyl, isopropyl, methoxy, ethoxy, trifluoromethyl, methoxycarbonyl, ethoxycarbonyl or propoxycarbonyl, and
R$^3$ represents phenyl which is unsubstituted or substituted by fluorine, chlorine trifluoromethyl, trifluoromethoxy, alkyl having up to 4 carbon atoms, alkoxy having up to 4 carbon atoms, cyano or alkoxycarbonyl having up to 4 carbon atoms, or represents pentafluorophenyl, or represents a straight-chain or branched alkyl, having up to 6 carbon atoms, which is unsubstituted or substituted by fluorine, chlorine, or phenyl,
or a physiologically acceptable salt thereof.

2. A method according to claim 1, wherein the phenylsulfonamide is selected from the group consisting of N-[4-(quinolin-2-yl-methoxy)phenyl]butanesulphonamide and N-[4-quinolin-2-yl-methoxy)phenyl]-1-methyl-butanesulphonamide.

3. A method for treating or preventing allergies, bronchitis, inflammations of the respiratory tract; or dermatosis in a human or animal patient which comprises administering to such patient an amount effective therefor a phenyl-sulphonamide of the formula

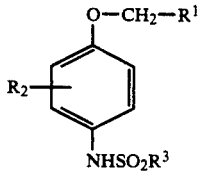

wherein
R$^1$ represents a quinolyl radical which is unsubstituted or substituted by fluorine, chlorine, alkyl having up to 4 carbon atoms, alkoxy having up to 4 carbon atoms or by trifluoromethyl,
R$^2$ represents hydrogen, cyano, fluorine, chlorine, methyl, ethyl, propyl, isopropyl, methoxy, ethoxy, trifluoromethyl, methoxycarbonyl, ethoxycarbonyl or propoxycarbonyl, and
R$^3$ represents phenyl which is unsubstituted or substituted by fluorine, chlorine, trifluoromethyl, trifluoromethoxy, alkyl having up to 4 carbon atoms, alkoxy having up to 4 carbon atoms, cyano or alkoxycarbonyl having up to 4 carbon atoms, or represents pentafluorophenyl, or represents a straight-chain or branched alkyl, having up to 6 carbon atoms, which is unsubstituted or substituted by fluorine, chlorine, or phenyl,
or a physiologically acceptable salt thereof.

4. A method according to claim 3, wherein the phenylsulfonamide is selected from the group consisting of N-[4-(quinolin-2-yl-methoxy)phenyl]butanesulphonamide and N-[4-quinolin-2-yl-methoxy)phenyl]-1-methyl-butanesulphonamide.

* * * * *

UNITED STATES PATENT AND TRADEMARK OFFICE
CERTIFICATE OF CORRECTION

PATENT NO. : 5,202,336
DATED : April 13, 1993
INVENTOR(S) : Mohrs et al.

It is certified that error appears in the above-identified patent and that said Letters Patent is hereby corrected as shown below:

| | |
|---|---|
| Title Page | OTHER REFERENCES: Insert -- Musser et al. Chem. Abstr Vol. 106 Entry 18377v abstracting E.P. 181568. -- |
| Col. 54, line 12 | Delete " fluoride " and substitute -- fluorine, -- |
| Col. 54, lines 17-18 | Delete " ethoxycarbyonyl " and substitute -- ethoxycarbonyl -- |
| Col. 54, line 19 | After " chlorine " insert -- , -- |
| Col. 54, line 33 | After " tract " delete " ; " |

Signed and Sealed this

Thirtieth Day of August, 1994

Attest:

BRUCE LEHMAN

*Attesting Officer*  *Commissioner of Patents and Trademarks*